(12) United States Patent
Doyle et al.

(10) Patent No.: US 7,470,268 B2
(45) Date of Patent: *Dec. 30, 2008

(54) HAND-ACTUATED ARTICULATING SURGICAL TOOL

(75) Inventors: Mark C. Doyle, San Diego, CA (US); Jimmy C. Caputo, Carlsbad, CA (US)

(73) Assignee: Allegiance Corporation, McGaw Park, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/352,899

(22) Filed: Feb. 13, 2006

(65) Prior Publication Data

US 2006/0195071 A1    Aug. 31, 2006

Related U.S. Application Data

(63) Continuation of application No. 10/996,872, filed on Nov. 23, 2004, now abandoned, which is a continuation of application No. 10/388,795, filed on Mar. 12, 2003, now abandoned, which is a continuation of application No. 09/910,482, filed on Jul. 18, 2001, now Pat. No. 6,607,475.

(60) Provisional application No. 60/219,593, filed on Jul. 20, 2000.

(51) Int. Cl.
   *A61B 17/00* (2006.01)
(52) U.S. Cl. .......................................... 606/1; 606/205
(58) Field of Classification Search ........................ None
   See application file for complete search history.

(56) References Cited

U.S. PATENT DOCUMENTS

| | | | |
|---|---|---|---|
| 2,426,695 A | 9/1947 | Kremiller | |
| 3,642,159 A | 2/1972 | Askins | |
| 3,702,535 A | 11/1972 | House | |
| 4,122,678 A | 10/1978 | Wilson | |
| 4,167,792 A | 9/1979 | Carnegie | |
| 4,485,817 A | 12/1984 | Swiggett | |
| 4,488,523 A | 12/1984 | Shichman | |
| 4,721,099 A | 1/1988 | Chikama | |
| 4,832,473 A | 5/1989 | Ueda | |
| 4,848,338 A | 7/1989 | De Satnick et al. | |
| 4,890,602 A | 1/1990 | Hake | |

(Continued)

FOREIGN PATENT DOCUMENTS

WO    WO 98/24017    6/1998

*Primary Examiner*—Thor S Campbell
(74) *Attorney, Agent, or Firm*—Arent Fox LLP

(57) ABSTRACT

A double cylinder system is disclosed, comprising at least one controller being adapted to transmit hydraulic control signals; at least one slave being in fluid communication with the controller and being configured to respond to the hydraulic control signals transmitted by the controller; and at least one control line providing hydraulic communication between the controller and the slave. Also disclosed is a surgical device, comprising at least one controller located at a proximal end of the device, the controller being adapted to transmit hydraulic control signals; at least one manipulator, the manipulator being configured to be controlled by a human hand and to actuate the controller; at least one slave located at a distal end of the device, the slave being in fluid communication with the controller and being configured to respond to the hydraulic control signals transmitted by the controller; and at least one control line providing hydraulic communication between the controller and the slave.

15 Claims, 26 Drawing Sheets

U.S. PATENT DOCUMENTS

| | | | |
|---|---|---|---|
| 4,946,329 A | 8/1990 | Krueger | |
| 5,112,184 A | 5/1992 | Tapper et al. | |
| 5,179,934 A | 1/1993 | Nagayoshi et al. | |
| 5,201,743 A | 4/1993 | Haber et al. | |
| 5,217,003 A | 6/1993 | Wilk | |
| 5,275,614 A | 1/1994 | Haber et al. | |
| 5,282,806 A | 2/1994 | Haber et al. | |
| 5,290,249 A | 3/1994 | Foster et al. | |
| 5,312,391 A | 5/1994 | Wilk | |
| 5,361,583 A | 11/1994 | Huitema | |
| 5,368,015 A | 11/1994 | Wilk | |
| 5,456,684 A | 10/1995 | Schmidt et al. | |
| 5,496,317 A | 3/1996 | Goble et al. | |
| 5,575,799 A | 11/1996 | Bolanos et al. | |
| 5,599,350 A | 2/1997 | Schulze et al. | |
| 5,611,813 A | 3/1997 | Lichtman | |
| 5,618,307 A | 4/1997 | Donlon et al. | |
| 5,620,459 A | 4/1997 | Lichtman | |
| 5,626,595 A | 5/1997 | Sklar et al. | |
| 5,681,262 A | 10/1997 | Isse | |
| 5,700,261 A | 12/1997 | Brinkerhoff | |
| 5,746,740 A | 5/1998 | Nicholas | |
| 5,746,759 A | 5/1998 | Meade et al. | |
| 5,752,972 A | 5/1998 | Hoogeboom | |
| 5,762,458 A | 6/1998 | Wang et al. | |
| 5,779,727 A | 7/1998 | Orejola | |
| 5,791,231 A | 8/1998 | Cohn et al. | |
| 5,792,135 A | 8/1998 | Madhani et al. | |
| 5,797,900 A | 8/1998 | Madhani et al. | |
| 5,797,941 A | 8/1998 | Schulze et al. | |
| 5,807,376 A | 9/1998 | Viola et al. | |
| 5,807,377 A | 9/1998 | Madhani et al. | |
| 5,807,378 A | 9/1998 | Jensen et al. | |
| 5,814,038 A | 9/1998 | Jensen et al. | |
| 5,820,623 A | 10/1998 | Ng | |
| 5,833,656 A | 11/1998 | Smith et al. | |
| 5,855,583 A | 1/1999 | Wang et al. | |
| 5,876,410 A | 3/1999 | Petillo | |
| 5,931,832 A | 8/1999 | Jensen | |
| 5,971,976 A | 10/1999 | Wang et al. | |
| 5,976,122 A | 11/1999 | Madhani et al. | |
| 6,001,108 A | 12/1999 | Wang et al. | |
| 6,007,550 A | 12/1999 | Wang et al. | |
| 6,017,358 A | 1/2000 | Yoon et al. | |
| 6,024,695 A | 2/2000 | Taylor et al. | |
| 6,063,095 A | 5/2000 | Wang et al. | |
| 6,099,536 A | 8/2000 | Petillo | |
| 6,102,850 A | 8/2000 | Wang et al. | |
| 6,102,909 A | 8/2000 | Chen et al. | |
| 6,131,480 A | 10/2000 | Yoneyama | |
| 6,132,368 A | 10/2000 | Cooper | |
| 6,132,441 A | 10/2000 | Grace | |
| 6,168,634 B1 | 1/2001 | Shmitz | |
| 6,179,837 B1 | 1/2001 | Hooven | |
| 6,197,017 B1 | 3/2001 | Brock et al. | |
| 6,201,984 B1 | 3/2001 | Funda et al. | |
| 6,206,903 B1 | 3/2001 | Ramans | |
| 6,223,100 B1 | 4/2001 | Green | |
| 6,244,809 B1 | 6/2001 | Wang et al. | |
| 6,246,200 B1 | 6/2001 | Blumenkranz et al. | |
| 6,296,635 B1 | 10/2001 | Smith et al. | |
| 6,309,397 B1 | 10/2001 | Julian et al. | |
| 6,312,435 B1 | 11/2001 | Wallace et al. | |
| 6,331,181 B1 | 12/2001 | Tierney et al. | |
| 6,346,072 B1 | 2/2002 | Cooper | |
| 6,361,534 B1 | 3/2002 | Chen et al. | |
| 6,371,952 B1 | 4/2002 | Madhani et al. | |
| 6,391,029 B1 | 5/2002 | Hooven et al. | |
| 6,398,726 B1 | 6/2002 | Ramans et al. | |
| 6,424,885 B1 | 7/2002 | Niemeyer et al. | |
| 6,432,112 B2 | 8/2002 | Brock et al. | |
| 6,434,329 B1 | 8/2002 | Dube et al. | |
| 6,441,577 B2 | 8/2002 | Blumenkranz et al. | |
| 6,468,265 B1 | 10/2002 | Evans et al. | |
| 6,488,265 B2 | 12/2002 | Laskaris et al. | |
| 6,491,691 B1 | 12/2002 | Morley et al. | |
| 6,491,701 B2 * | 12/2002 | Tierney et al. | 606/130 |
| 6,554,844 B2 | 4/2003 | Lee et al. | |
| 6,574,355 B2 | 6/2003 | Green | |
| 6,607,475 B2 * | 8/2003 | Doyle et al. | 600/1 |
| 6,620,174 B2 | 9/2003 | Jensen et al. | |
| 6,622,980 B2 | 9/2003 | Boucher et al. | |
| 6,665,554 B1 | 12/2003 | Charles et al. | |
| 6,671,581 B2 | 12/2003 | Niemeyer et al. | |
| 6,676,669 B2 | 1/2004 | Charles et al. | |
| 6,676,684 B1 | 1/2004 | Morley et al. | |
| 6,692,485 B1 | 2/2004 | Brock et al. | |
| 6,702,805 B1 | 3/2004 | Stuart | |
| 6,723,087 B2 | 4/2004 | O'Neill et al. | |
| 6,723,106 B1 | 4/2004 | Charles et al. | |
| 6,731,988 B1 | 5/2004 | Green | |
| 6,746,443 B1 | 6/2004 | Morley et al. | |
| 6,755,338 B2 | 6/2004 | Hahnen et al. | |
| 6,764,445 B2 | 7/2004 | Ramans et al. | |
| 6,770,081 B1 | 8/2004 | Cooper et al. | |
| 6,776,783 B1 | 8/2004 | Frantzen et al. | |
| 6,783,524 B2 | 8/2004 | Anderson et al. | |
| 6,786,896 B1 | 9/2004 | Madhani et al. | |
| 6,788,018 B1 | 9/2004 | Blumenkranz | |
| 6,788,999 B2 | 9/2004 | Green | |
| 6,817,974 B2 | 11/2004 | Cooper et al. | |
| 6,827,725 B2 | 12/2004 | Batchelor et al. | |
| 6,830,174 B2 | 12/2004 | Hillstead et al. | |
| 6,840,938 B1 | 1/2005 | Morley et al. | |
| 6,843,793 B2 | 1/2005 | Brock et al. | |
| 6,850,817 B1 | 2/2005 | Green | |
| 6,860,878 B2 | 3/2005 | Brock | |
| 6,866,671 B2 | 3/2005 | Tierney et al. | |
| 6,879,880 B2 | 4/2005 | Nowlin et al. | |
| 6,902,560 B1 | 6/2005 | Morley et al. | |
| 6,936,042 B2 | 8/2005 | Wallace et al. | |
| 6,949,106 B2 | 9/2005 | Brock et al. | |
| 6,963,792 B1 | 11/2005 | Green | |
| 6,991,627 B2 | 1/2006 | Madhani et al. | |
| 6,994,708 B2 | 2/2006 | Manzo | |
| 6,999,852 B2 | 2/2006 | Green | |
| 7,006,895 B2 | 2/2006 | Green | |
| 7,048,745 B2 | 5/2006 | Tierney et al. | |
| 7,063,697 B2 | 6/2006 | Slater | |
| 7,083,615 B2 | 8/2006 | Peterson et al. | |
| 7,083,618 B2 | 8/2006 | Couture et al. | |
| 7,090,683 B2 | 8/2006 | Brock et al. | |
| 7,101,371 B2 | 9/2006 | Dycus et al. | |
| 7,107,124 B2 | 9/2006 | Green | |
| 7,108,688 B2 | 9/2006 | Jensen | |
| 7,125,403 B2 | 10/2006 | Julian et al. | |
| 7,155,315 B2 | 12/2006 | Niemeyer et al. | |
| 7,155,316 B2 | 12/2006 | Sutherland et al. | |
| 7,169,141 B2 | 1/2007 | Brock et al. | |
| 7,204,844 B2 | 4/2007 | Jensen et al. | |
| 7,246,734 B2 | 7/2007 | Shelton, IV | |
| 7,248,944 B2 | 7/2007 | Green | |
| 7,250,028 B2 | 7/2007 | Julian et al. | |
| 7,252,660 B2 | 8/2007 | Kunz | |
| 7,276,065 B2 | 10/2007 | Morley et al. | |
| 7,297,142 B2 | 11/2007 | Brock | |
| 7,306,597 B2 | 12/2007 | Manzo | |
| 7,316,681 B2 | 1/2008 | Madhani et al. | |
| 7,320,700 B2 | 1/2008 | Cooper et al. | |
| 2002/0120252 A1 | 8/2002 | Brock et al. | |
| 2003/0083673 A1 | 5/2003 | Tierney et al. | |
| 2003/0109877 A1 | 6/2003 | Morley et al. | |
| 2003/0135204 A1 | 7/2003 | Lee et al. | |
| 2003/0216715 A1 | 11/2003 | Moll et al. | |

| | | | | | |
|---|---|---|---|---|---|
| 2003/0236549 A1 | 12/2003 | Bonadio et al. | 2007/0012135 A1 | 1/2007 | Tierney et al. |
| 2004/0039485 A1 | 2/2004 | Niemeyer et al. | 2007/0021776 A1 | 1/2007 | Jensen et al. |
| 2004/0193146 A1 | 9/2004 | Lee et al. | 2007/0088340 A1 | 4/2007 | Brock et al. |
| 2005/0021018 A1 | 1/2005 | Anderson et al. | 2007/0093792 A1 | 4/2007 | Julian et al. |
| 2005/0149003 A1 | 7/2005 | Tierney et al. | 2007/0123855 A1 | 5/2007 | Morley et al. |
| 2005/0215983 A1 | 9/2005 | Brock | 2007/0233052 A1 | 10/2007 | Brock |
| 2005/0216033 A1 | 9/2005 | Lee et al. | 2008/0033453 A1 | 2/2008 | Brock |
| 2005/0228440 A1 | 10/2005 | Brock et al. | | | |
| 2005/0240178 A1 | 10/2005 | Morley et al. | | | |

\* cited by examiner

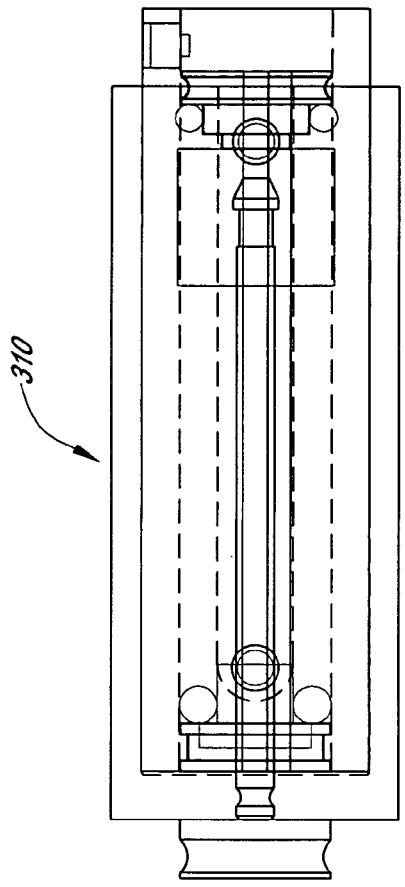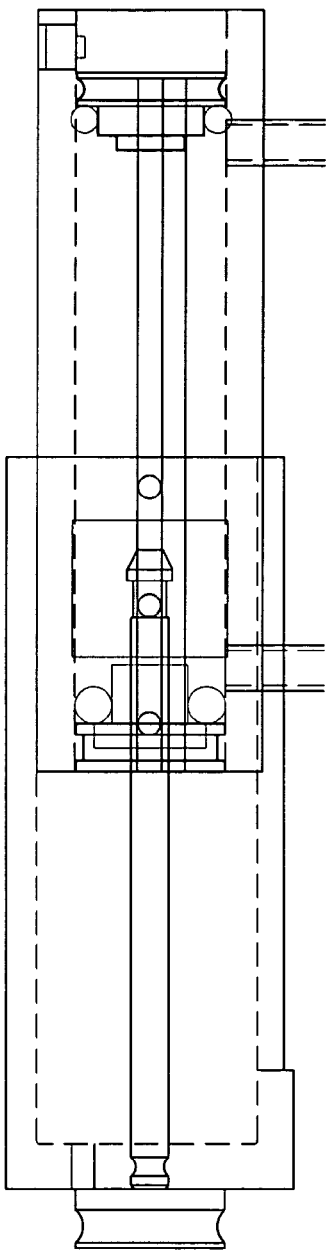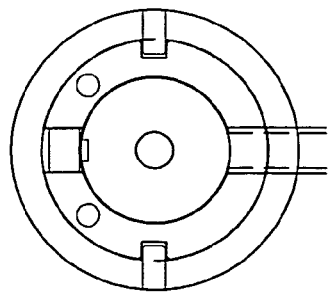
FIG. 3A
FIG. 3B
FIG. 3C

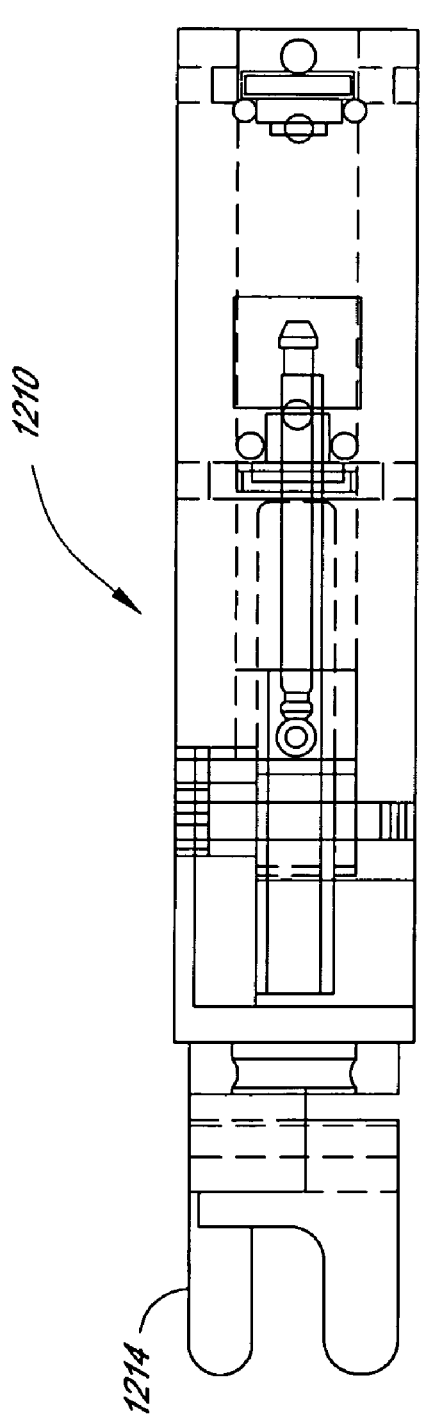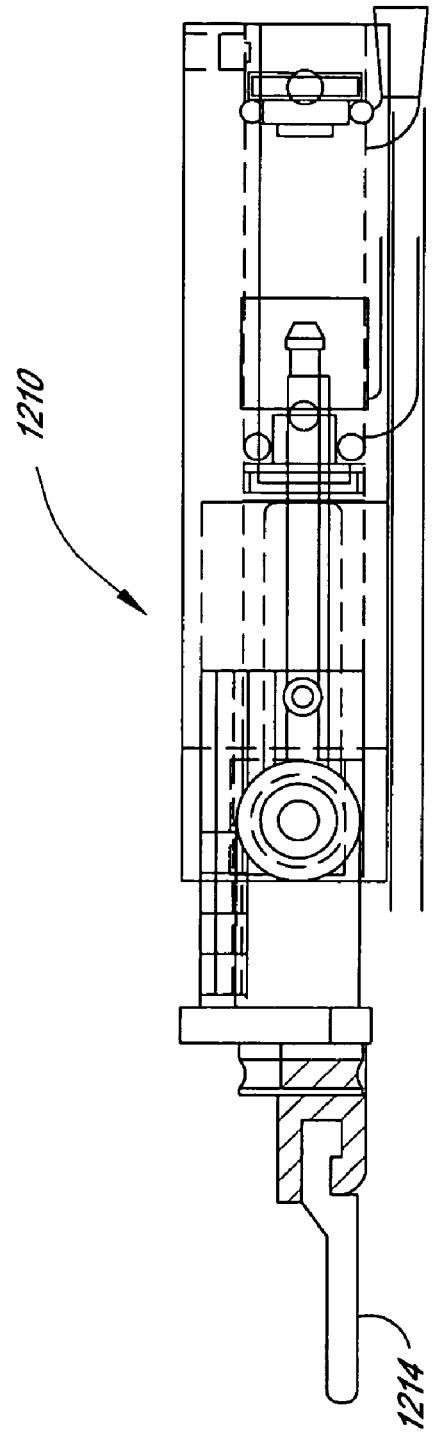

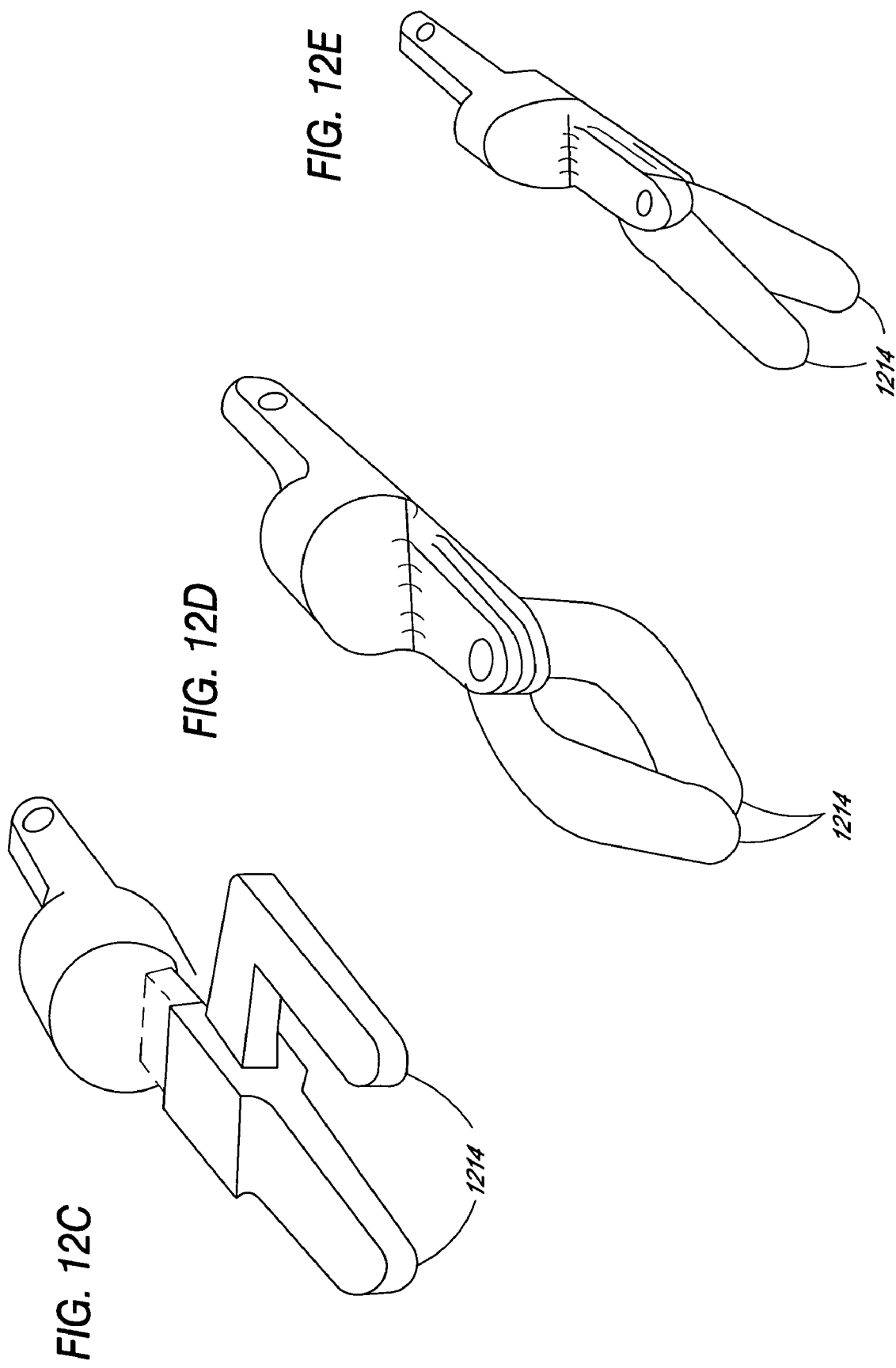

HAND-ACTUATED ARTICULATING SURGICAL TOOL

RELATED APPLICATIONS

This application is a continuation of U.S. application Ser. No. 10/996,872, filed on Nov. 23, 2004, now abandoned by Doyle et al., and entitled "HAND-ACTUATED ARTICULATING SURGICAL TOOL," which in turn is a continuation of U.S. application Ser. No. 10/388,795, filed on Mar. 12, 2003, now abandoned by Doyle et al., and entitled "HAND-ACTUATED ARTICULATING SURGICAL TOOL," which in turn is a continuation of U.S. application Ser. No. 09/910,482, filed on Jul. 18, 2001, by Doyle et al., and entitled "HAND-ACTUATED ARTICULATING SURGICAL TOOL," now U.S. Pat. No. 6,607,475, issued on Aug. 19, 2003, which in turn claims priority to the U.S. Provisional Application Ser. No. 60/219,593, filed Jul. 20, 2000, by Doyle et al., and entitled "HAND-ACTUATED ARTICULATING SURGICAL TOOL," all of which are incorporated by reference herein in their entirety, including any drawings.

FIELD OF THE INVENTION

The invention relates generally to surgical instruments. More particularly, the invention relates to a hand-actuated articulating surgical tool for use in minimally invasive surgical procedures.

BACKGROUND OF THE INVENTION

Current laparoscopic surgical tools are limited in accessibility of certain regions of the human body. Existing tools can perform invasive surgery without making a substantial incision, but these tools are incapable of bending within the body to reach, for example, the backside of the human heart.

Additionally, existing tools rely on use of cables to manipulate the surgical tip of the tool. These tools have the disadvantage of requiring extensive sterilization of the internal components. The cleaning of internal metal cables can be a lengthy and expensive process. This process must be repeated prior to each procedure. Alternatively, disposable components may be used with a substantial increase in recurring costs.

In order for a surgeon to perform a surgical procedure on an active organ, such as the heart, current tools require the organ to be arrested. For example, in order to operate on a small portion of the heart, the patient must be placed on an artificial support system while the heart is temporarily stopped for the surgery. This requires additional equipment such as the artificial support system, substantially increasing the cost of the procedure. Also, the recovery period for the patient is substantially increased.

SUMMARY OF THE INVENTION

The present invention provides an apparatus for performing minimally invasive surgery while allowing articulation of the tool within the patient's body. Further, the present invention provides a surgical tool that is simple and inexpensive to sterilize and reuse. Another embodiment of the invention allows a surgeon to operate on a portion of an organ, for example, the heart, without the need for arresting the entire organ.

One embodiment of the present invention is a surgical device, comprising at least one controller located at the proximal end of the device adapted to transmit hydraulic control signals. At least one manipulator, configured to be controlled by a human finger actuates the controller. At least one slave, located at the distal end of the device, is in fluid communication with the controller and is configured to respond to the hydraulic control signals transmitted by the controller. A control line provides hydraulic communication between the controller and the slave.

In a preferred embodiment, the controller comprises a control cavity and a piston within the control cavity. The piston divides the control cavity into a first control cavity portion and a second control cavity portion and prevents communication between the two portions. The slave comprises a slave cavity and a piston within the slave cavity that divides the slave cavity into first and second portions and prevents communication between the two portions. The control line provides hydraulic communication between the first control cavity portion and the first slave cavity portion. A second control line provides hydraulic communication between the second control cavity portion and the second slave cavity portion.

In another embodiment, the surgical device comprises a control portion located at the proximal end having a plurality of controllers, each controller being adapted to transmit hydraulic control signals. A plurality of manipulators, configured to be controlled by a human finger, actuate a corresponding controller. A slave portion located at the distal end of the device comprises a plurality of slaves. Each slave is in communication with a corresponding controller, and responds to the hydraulic control signals transmitted by the controller. A surgical tip is manipulated by the slaves in response to the hydraulic control signals. Control lines provide communication between the controllers and the slaves. In a preferred embodiment, an outer sleeve envelops the control lines.

The device can also include an articulating portion. The articulating portion comprises a spring bar on one side and a plurality of pockets on an opposing side. The pockets are configured to receive a hydraulic fluid and expand, causing the device to bend as desired. In a preferred embodiment, the device includes a stabilizer having a rigid shaft and a stabilizing plate. The stabilizing plate has an access cutout, and is configured to pivot about the end of the shaft. The shaft can include an articulating portion, if desired.

BRIEF DESCRIPTION OF THE DRAWINGS

The features, objects and advantages of the present invention will become more apparent from the detailed description set forth below when taken in conjunction with the drawings in which like references identify correspondingly throughout, and wherein:

FIG. 2 is a detailed drawing of one embodiment of the control portion of the invention.

FIG. 3A is a detailed drawing of an embodiment of a control cylinder. FIG. 3B shows the cylinder's retracted position, while FIG. 3C shows the cylinder's extended position.

FIG. 4 is a detailed drawing of an embodiment of a hydraulic extend module. FIG. 4A shows the module's retracted position, while

FIG. 7A is top view and FIG. 7B is side view.

FIG. 9 depicts various arrangements of the modules.

FIG. 10 shows an embodiment of the tubing management. FIG. 10B shows the position of the guide tubes with respect to the bend module, while

FIG. 12 shows an embodiment of the tissue restraint module. FIG. 12A is top view while FIG. 12B is side view. FIGS. 12C-E show various embodiments of the separable tynes of the tissue restraint modules.

DETAILED DESCRIPTION OF THE INVENTION

Certain embodiments of the invention will now be described in detail with reference to the figures.

Figure 1:
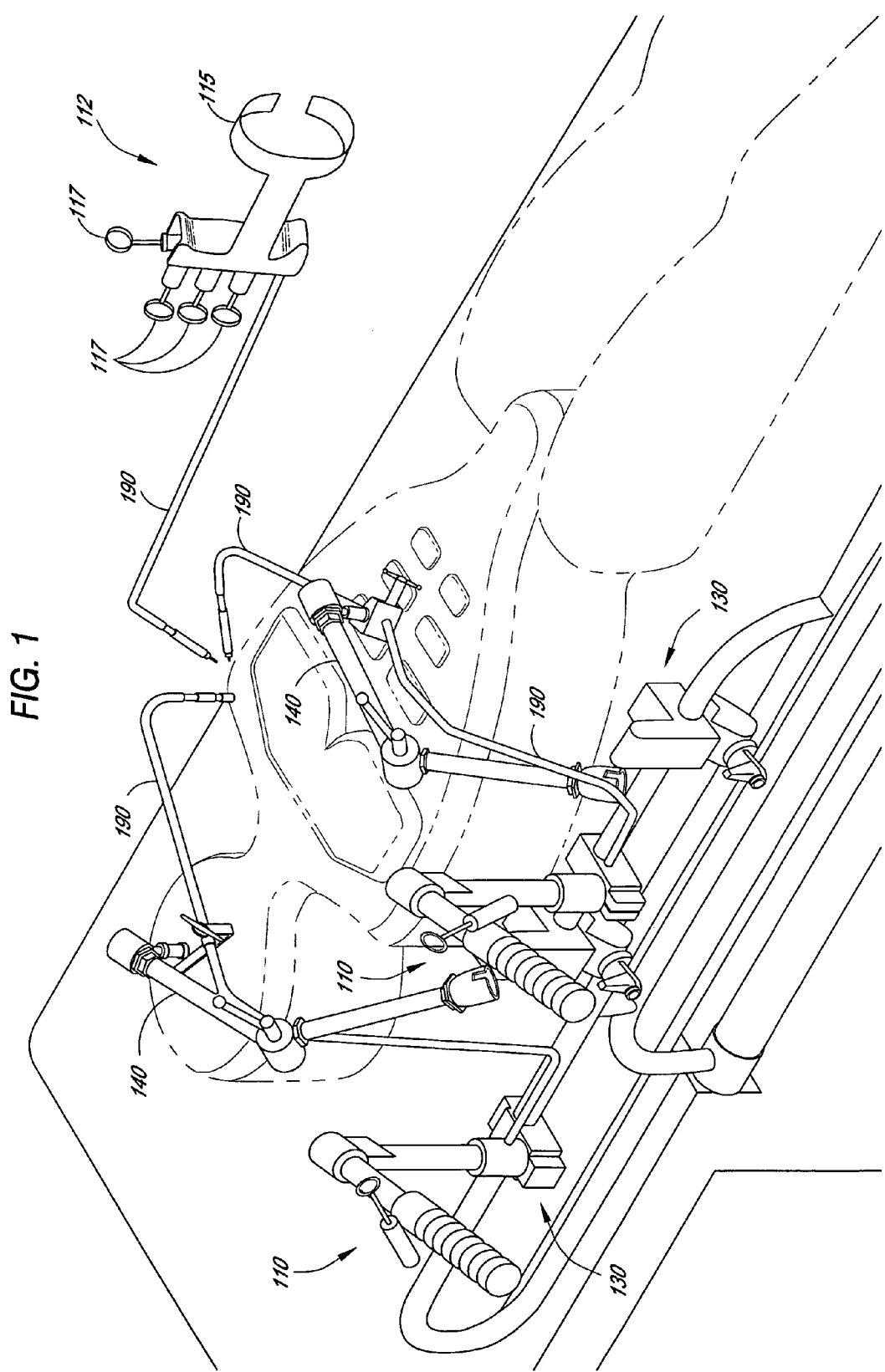
FIG. 1 is an overview of one embodiment of the invention.

FIG. 1 shows a surgical tool according to the present invention. The tool has a control portion 110, 112 at the proximal end of the device and a slave portion 120 at the distal end of the device. As used herein, "proximal" refers to the part of the device that remains outside the patient's body, closest to the user. "Distal" refers to the end inserted into the patient, farthest away from the user. As with a specific component of the device, "proximal" refers to the part of the component closest to the proximal end of the device, whereas "distal" refers to the part of the component closest to the distal end of the device. An intermediate portion 190 lies between the control portion 110 and the slave portion 120. The "slave portion," or the "distal end of the device," 120 is the portion of the device comprising the slave modules, i.e., the extend module, the bend module, the rotate module, and the grasp module, as each is described in greater detail below. Each portion will now be described in greater detail. The term "cannula" is used to refer to the portion of the device comprising both the intermediate portion 190 and the slave portion 120.

The control portion 110, 112 may be any device that can translate the movements of the user's hand and fingers into hydraulic, mechanical, or electrical signals to actuate the corresponding parts of the slave portion 120 of the device. For example, two such devices are shown in FIG. 1.

In certain embodiments, the control portion 110, 112 uses hydraulic fluid to transfer pressure from a control cylinder to a slave cylinder. The fluid is preferably sterilized distilled water, however a saline solution, a perfluorinated hydrocarbon liquid, or any other physiologically compatible fluid could also be used. A "physiologically compatible fluid" is a fluid that once exposed to tissues and organs, does not create any intolerable reaction, such as a rash or immune response, in the patient, and does not adversely interfere with the normal physiological function of the tissues or organs to which it is exposed. In addition, a physiologically compatible fluid can remain in a patient's body or in contact with a tissue or an organ without the need to remove the fluid.

In one embodiment, the control portion 112 clamps onto the arm of the user by way of a clamp 115. The control portion 112 features finger loops 117, into which the user inserts the user's fingers. By squeezing each finger loop 117, the user creates hydraulic pressure or an electrical signal that results in a corresponding motion at the distal end 120 of the device. The user may then "open" the squeezed finger to create the opposite motion.

Figure 3D:
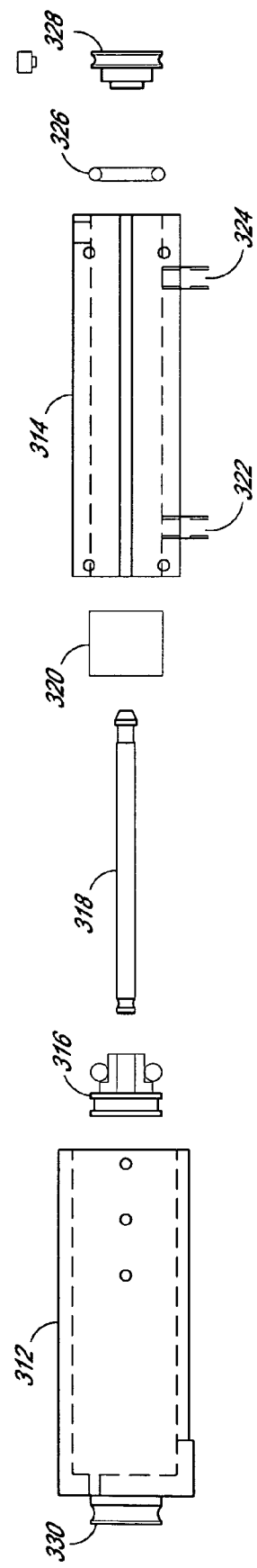
FIG. 3D shows the components of the control cylinder individually.

Each finger loop 117 is connected with a control cylinder 310 (shown in FIG. 3). The finger loop 117 should be large enough to allow comfortable insertion of a human finger. The finger loop 117 is connected to a longitudinal shaft. The shaft may be made of, for example, metal, ground glass, or ceramic. The shaft may be of any cross-sectional shape, but a circular cross-section is preferred. The cross-sectional size of the shaft, along with the material, are designed to provide sufficient stiffness for predictable control when the finger loop 117 is moved. The shaft slides through an opening in the end of the cylinder body. The interface between the shaft and the opening in the end of the cylinder body is formed to allow for smooth forward and backward movement of the shaft and preferably, at the same time, to provide a waterproof seal.

Another embodiment of the invention includes a control portion 110 that is clamped to the side of a surgical bed using clamps 130. In this embodiment, the user grasps the control portion 110 much in the same way that a motorcycle driver grasps the handles of a motorcycle. The user may turn the handles, push them in, pull them out, pivot them about their axes, or, with the aid of a thumb loop, squeeze them. As detailed below, each of these motions creates a corresponding motion at the distal end 120 of the device.

In another embodiment, the control portion 110 is clamped to an object other than the surgical bed, such as a table or a cart. In yet another embodiment, the control portion 110 is clamped to the user's arms or hand. In still another embodiment, the control portion 110 is held by the user, without it being clamped to anything.

Figure 2A:
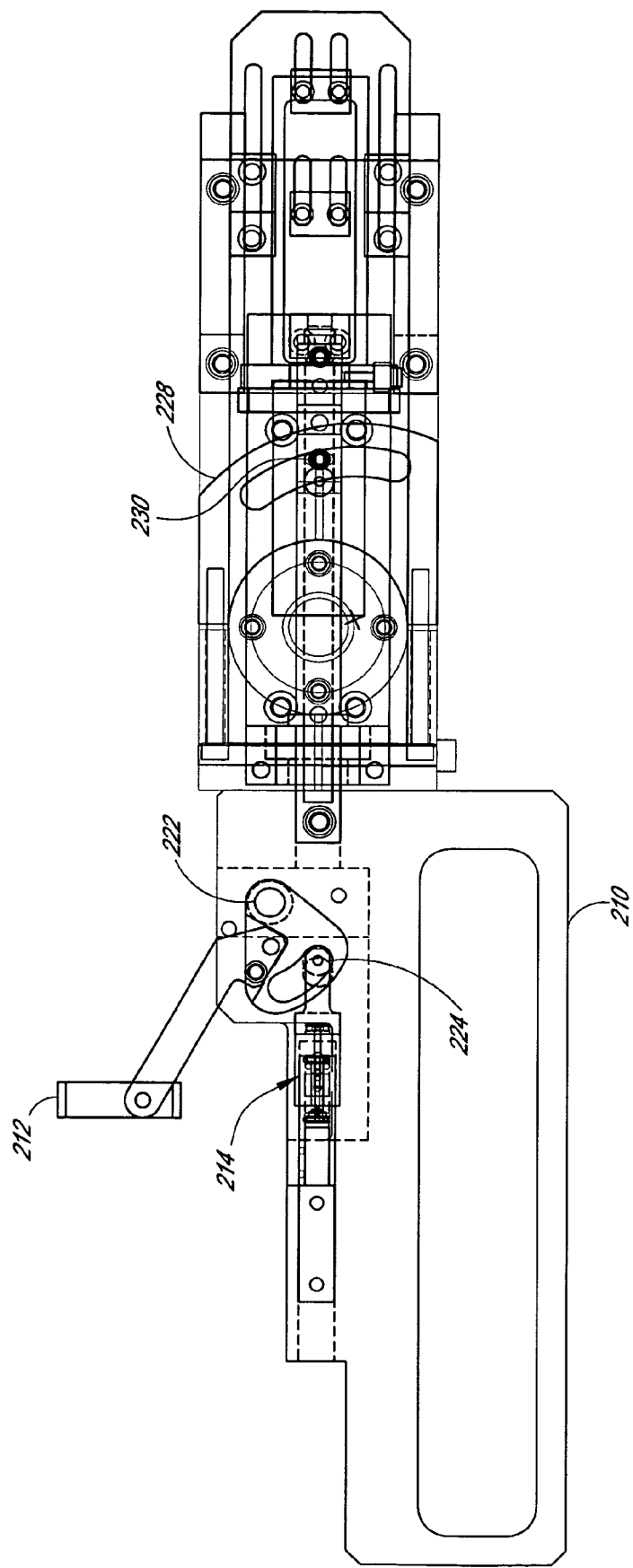
FIG. 2A is top view.

FIG. 2A shows the top view of the control portion 110. A handle 210 is provided for the user's fingers to pass through, while the user's thumb is inserted through a thumb loop 212. The handle 210 may exhibit ridges on the inside of the open loop in order to more comfortably accommodate a user's fingers.

The movements of the control portion 110 are translated into hydraulic motion through the use of control cylinders 214, 216, 218, 220. When the user squeezes the thumb loop 212 towards the handle 210, a bend cam 222 is turned about a vertical axis. The bend cam 222 is shown in FIG. 2D. As the bend cam 222 turns, a roller 224 is pushed towards the back of the handle. The roller 224 is connected to an outer cylinder 312 of a control cylinder 214 via a shaft 318. The backward movement of the shaft 318 extends a piston 320 backwards, thereby creating the hydraulic pressure needed to actuate a slave cylinder in the distal end 120 of the device. The function of a control cylinder and its connection to a slave cylinder are discussed in greater detail below. In one embodiment of the invention, the squeezing of the thumb loop actuates a grasp function at the distal end 120.

The control portion 110 may be attached to the side of a surgical bed using a clamp 130. However, the control portion is free to rotate about a vertical axis 226, shown in FIG. 2B. The rotation of the control portion 110 about the axis 226 causes a roller 230 to move within a bend cam 228. The bend cam 228 is shown in FIG. 2E. The roller 230 is connected to an outer cylinder 312 of a control cylinder 220 via a shaft 318. The forward movement of the shaft 318 extends the piston 320 forward, thereby creating the hydraulic pressure needed to actuate a slave cylinder in the distal end 120 of the device. In one embodiment of the invention, the turning of the handle results in a rotation of the distal end 120 of the device through a rotate module, described in detail below.

A user may also push the handle 210 forward, in which case, the top portion of the control portion 110 moves forward over a slide 232. The slide 232 is connected to an outer cylinder 312 of a control cylinder 218 via an attachment point 330. The outer cylinder 312 is in turn attached to the piston 320 via a shaft 318. The forward movement of the shaft 318 extends the piston 320 forward, thereby creating the hydraulic pressure needed to actuate a slave cylinder in the distal end 120 of the device. In one embodiment of the invention, the forward movement of the handle results in an extension of the distal end 120 of the device through an extension module, described in detail below.

Figure 2B:
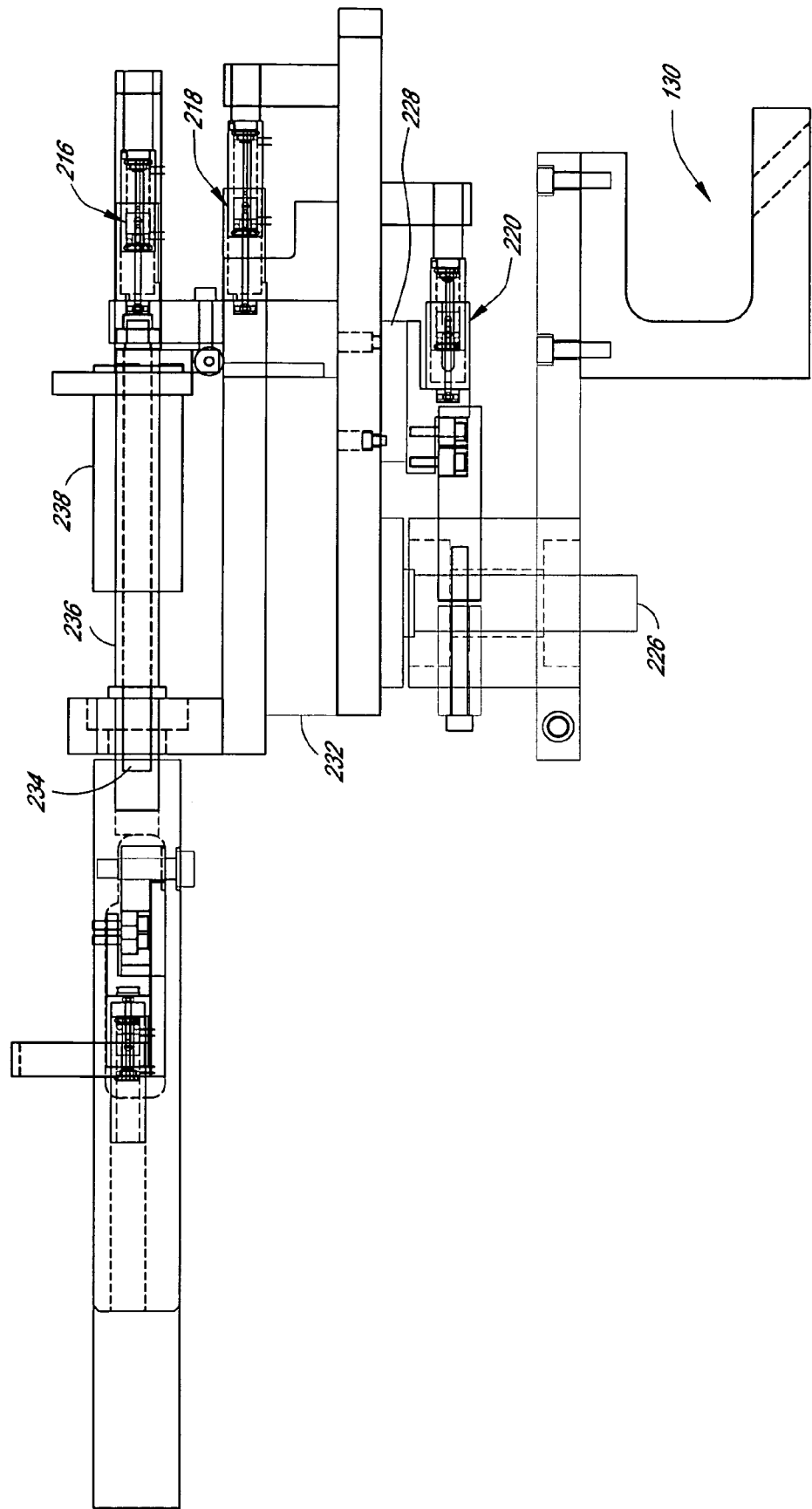
FIG. 2B is side view.
Figure 2C:
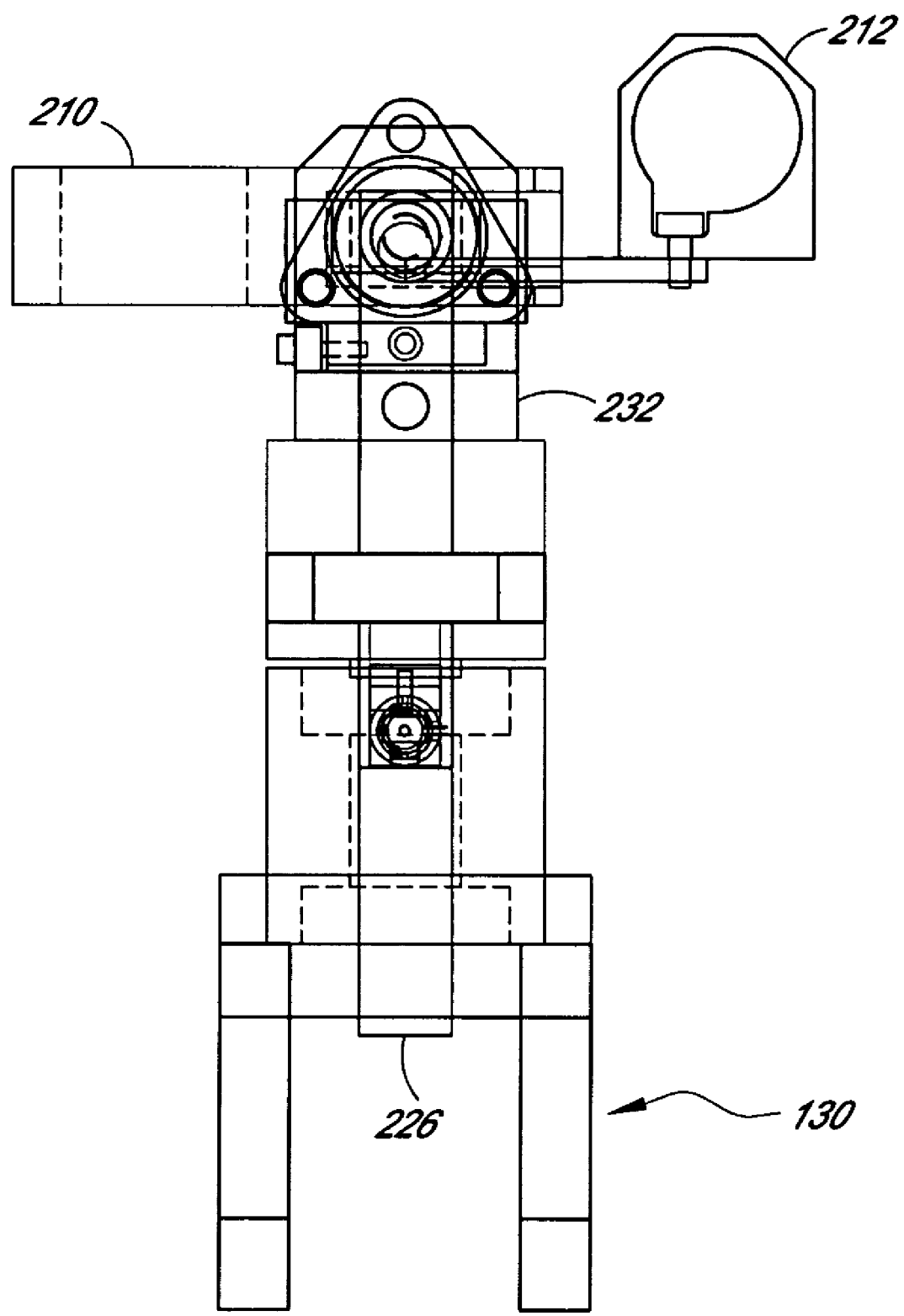
FIG. 2C is front view.
Figure 2E:
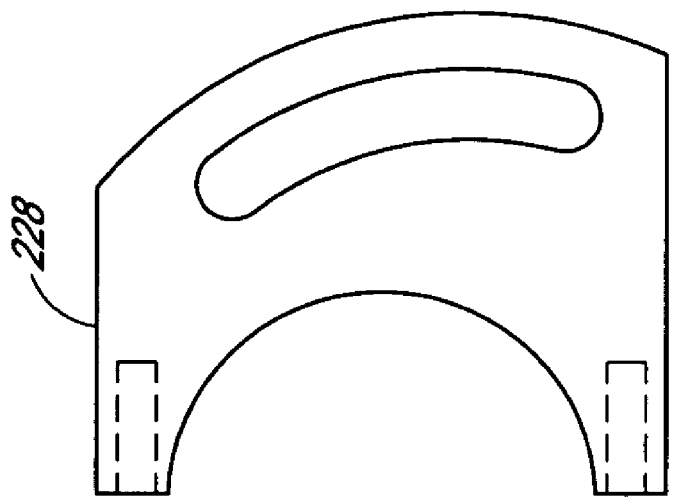
FIG. 2E shows a top view of a bend cam.
Figure 2D:
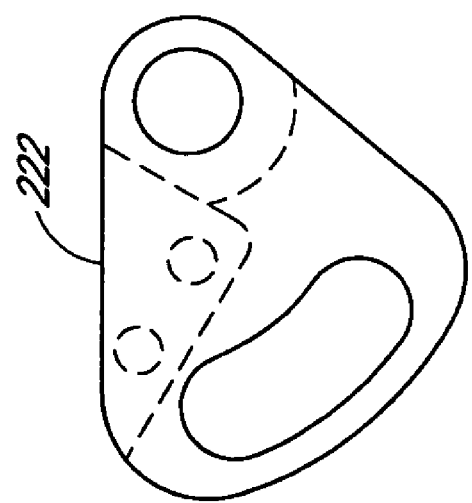
FIG. 2D shows a top view of a grasp cam.

The handle part of the control portion 110 may also rotate along a longitudinal axis coinciding with the shaft 234, as shown in FIG. 2B. In certain embodiments of the invention, the turning of the handle part causes a screw 236 to rotate within a nut 238. In some embodiments of the invention, the screw 236 is stationary and the nut 238 is mobile, whereas in other embodiments of the invention, the screw 236 is mobile and the nut 238 is stationary. The movement of the screw 236 within the nut 238 causes the mobile unit to move linearly with respect to the stationary unit. The mobile unit, whether the screw or the nut, is connected to an outer cylinder 312 of a control cylinder 216 via an attachment point 330. The outer cylinder 312 is in turn attached to the piston 320 via a shaft 318. The forward movement of the shaft 318 extends the piston 320 forward, while the backward movement of the shaft 318 pulls the piston 320 backward. The forward and backward motion of the piston 320 creates the hydraulic pressure needed to actuate a slave cylinder in the distal end 120 of the device. In some embodiments of the invention, rotation of the handle part results in the rotation of the distal end 120 of the device through a rotation module, described in detail below.

In certain embodiments of the invention, the movements of the different parts of the control portion 110 creates electrical signals that are sent through wires in the intermediate portion 190 to the slave cylinders in the distal end 120 of the device. The electrical signal is sufficient to actuate a motor in the corresponding slave cylinder, which in turn results in the slave module being actuated. Thus, for example, a forward movement of the handle 210 creates an electrical signal that actuates a motor in an extend module, which results in the extension of that module. Similarly, the rotation of the handle 210, the bending of the handle 210, and the squeezing of the thumb loop 212, result in the rotate module, the bend module, and the grasp module, respectively, being actuated. The slave modules having a motor are described in greater detail below.

Cylinders 214, 216, 218, and 220 are control cylinders. A typical control cylinder 310 is shown in its retracted position in FIG. 3A and in its extended position in FIG. 3B. The control cylinder 310 comprises an outer cylinder 312 and an inner cylinder 314. The inner cylinder 314 has a diameter that allows it to move within the outer cylinder 312. The outer cylinder 312 is connected to a shaft 318, which in turn is connected to the control portion 110 through the attachment point 330. The movements of the control portion 110, described above, causes the outer cylinder 312 to move longitudinally with respect to the stationary inner cylinder 314.

A piston 320, attached to a shaft 318, moves within the inner cylinder 314, within a distance defined by the two inlet points 322, 324 for the hydraulic fluid. The distal end of the shaft 318 is configured to be capable of attachment to the piston 320, while the proximal end of the shaft 318 is configured to be capable of attachment to the outer cylinder at a site close to the attachment point 330. The outer cylinder or the handle assembly may be provided with ratchet teeth. The ratchet teeth are adapted to engage with a locking mechanism to secure the piston 320 at a desired position relative to the cylinder body. Alternatively, a locking mechanism may employ a friction lock to secure the piston 320 at a desired position.

The piston 320 has a solid front face and is movable along the longitudinal axis of the inner cylinder 314. The front face of the piston 320 is identical in shape to the cross section of the cylindrical cavity. The outer surface of the piston 320 forms an airtight seal with the inner surface of the inner cylinder 314. Thus, the portion of the cavity on one side of the piston 320 does not communicate with the portion of the cavity on the other side of the piston 320. At the same time, the piston 320 must be allowed to move smoothly back and forth along the longitudinal axis of the inner cylinder 314.

The proximal end of the inner cylinder 314 is sealed with a seal 316, comprising an opening therethrough, through which the shaft 318 can slide. The distal end of the inner cylinder 314 is sealed with another seal 328, optionally comprising an O-ring 326.

Thus, in the extended position of the control cylinder 310, FIG. 3B, the piston 320 is at rest against the proximal seal 316. The hydraulic fluid is located in the inner cylinder 314 in front of the piston 320. When the control portion 110 is moved in a way described above, i.e., when the handle 210 is moved forward, the outer cylinder 312 moves forward, thereby moving the shaft 318 and the piston 320. Hydraulic fluid exits the inner cylinder 314 through an inlet 324, creating a hydraulic pressure at a point in the distal end 120 of the device. Additional hydraulic fluid, displaced from a slave cylinder, enters to the back of the piston 320 through another inlet 322, thereby keeping the volume of the hydraulic fluid in the system constant. When the control portion 110 is moved completely, the control cylinder 310 is in its retracted position, FIG. 3A. In this position, the piston 320 is at the distal end of the inner cylinder 314, resting against the distal seal 328. The hydraulic fluid is in the back of the piston 320. Those of skill in the art understand that although in the above discussion the piston 320 is described to move from the fully retracted position to the fully extended position, the piston 320 may move from any point along the two extremes to any other point along the two extremes, and thereby cause a corresponding movement in a slave cylinder.

The cannula 190 comprises hydraulic tubings, connecting the control cylinders of the control portion 110 with the slave cylinders at the distal end 120, and housings for the hydraulic tubings.

The distal end 120 comprises modular components. The components can be selected from, for example, an extend module, a rotate module, a bend module, and a grasp module. Other functions can be included as well and activated in the manner described in detail below. Each module is individually describe in greater detail below. The invention is adapted such that the user can pick the combination of modules and the quantity of each individual module that is best suitable for the user's needs and assemble them conveniently.

Figure 4A:
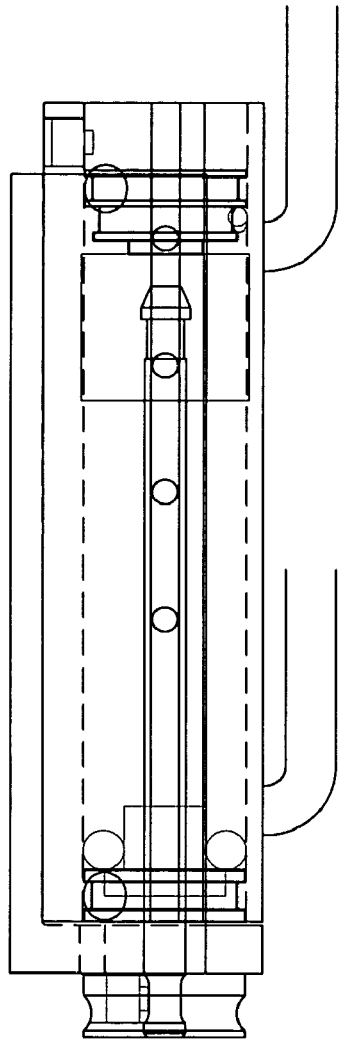
Figure 4C:
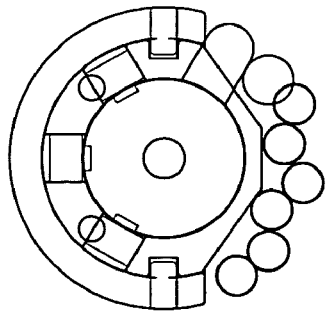
FIG. 4C shows the front view of the module.
Figure 4B:
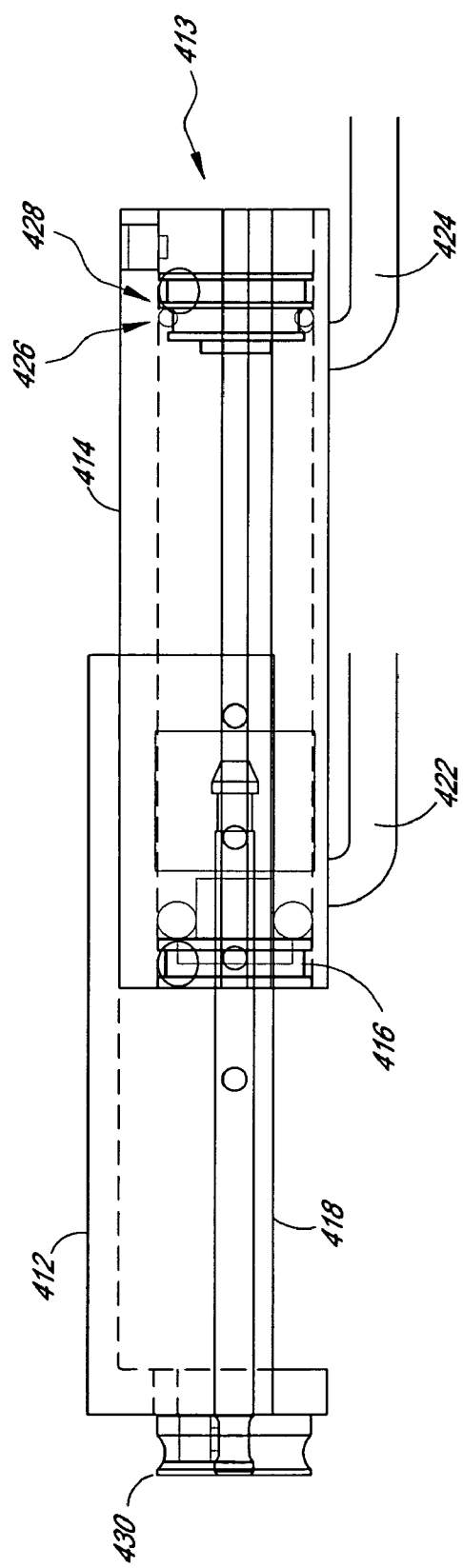
FIG. 4B shows the module's extended position.

The extend module 410 is depicted in both its retracted position, FIG. 4A, and extended position, FIG. 4B. The extend module 410 is identical in its construction to the control module 310; however, the function of the two are reversed. By applying hydraulic pressure using the control portion 110, hydraulic fluid enters the inner cylinder 414 pushing the piston 420 towards the distal end of the module and the distal seal 416. The shaft 418 moves through the distal seal 416, but it is attached to the outer cylinder 412 at the distal end of the outer cylinder 430. The movement of the piston 420 moves the outer cylinder 412 towards the distal end of the module, thereby extending the cannula. The hydraulic fluid present inside the inner cylinder 414 exits the inner cylinder 414 through the distal outlet 422. The proximal seal 428 prevents the leakage of hydraulic fluid from proximal end of the inner cylinder 414.

Additional modules can be attached to the extend module either at its distal end, through the distal attachment point 430, or at its proximal end, through the proximal attachment point 431.

Figure 4D:
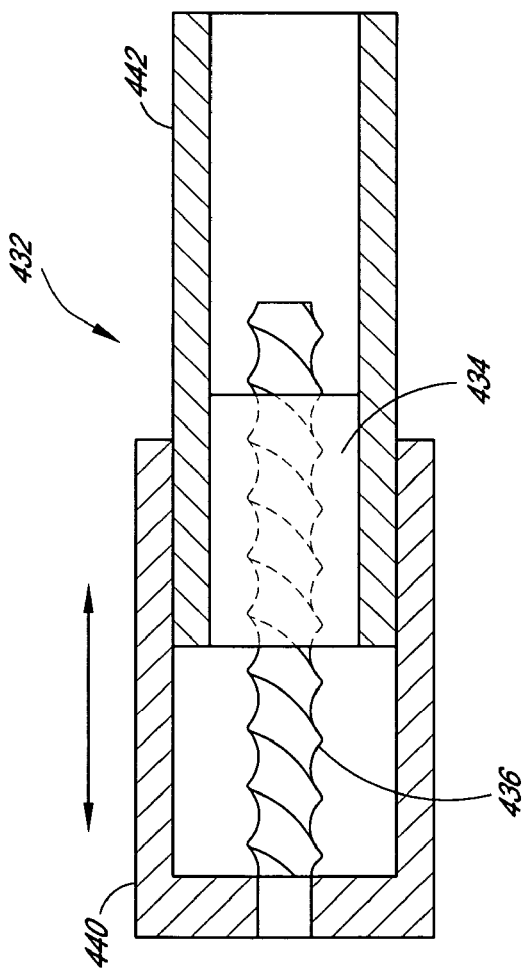
FIGS. 4D-E show two embodiments of an electrical extend module.

In another embodiment, the extend module may be extended using electrical power instead of hydraulic power. In this embodiment, by pushing forward on the handle 210 of the control portion 110, the user causes an electrical connection to be formed, whereby electrical signal is sent from the control portion 110 through wires in the intermediate portion 190 to the extend module 432, FIGS. 4D, 4E. The electrical signal causes an electrical motor 434 to turn. In one embodiment, FIG. 4D, a screw 436 is mounted within the motor 434. The turning of the motor 434 causes the screw to move outward, thereby causing the outer cylinder 440 to move away from the inner cylinder 442. In this embodiment, the motor is stationary, i.e., it is attached to the inner cylinder 442, whereas the screw is mobile, i.e., it moves with respect to the motor and the inner cylinder 442. The screw 436 is attached at its distal end to the outer cylinder 440.

Figure 4E:
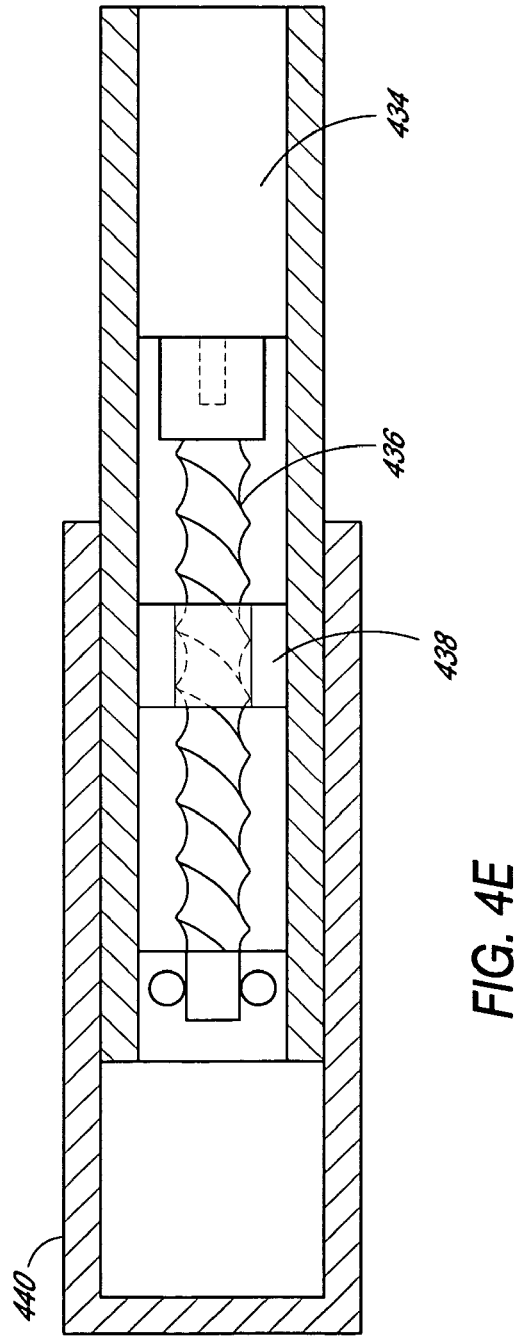

In another embodiment, FIG. 4E, the motor 434 causes the screw 436 to turn within a nut 438. The nut 438 is attached to the outer cylinder 440. The turning of the screw 436 causes the nut 438 to move with respect to the screw 436, thereby moving the outer cylinder 440 longitudinally with respect to the inner cylinder 442, causing the module to extend. In this embodiment, the motor 434 and the screw 436 are stationary with respect to the inner cylinder 442, whereas the nut 438 and the outer cylinder 440 are mobile.

Figure 5A:
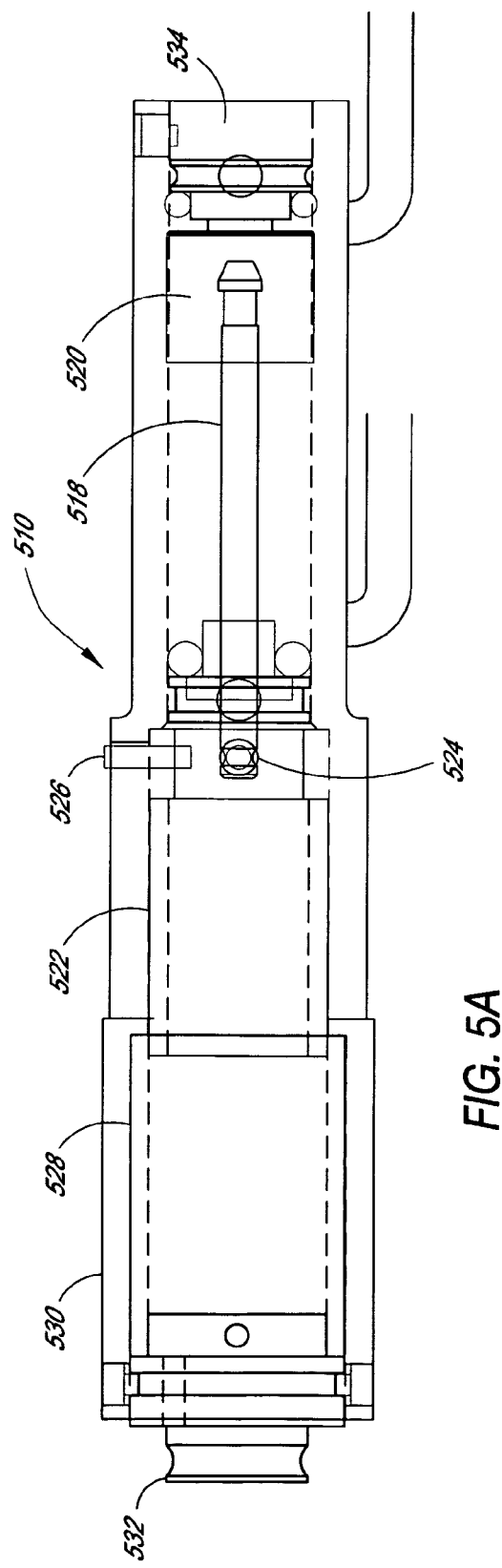
FIG. 5A is a detailed drawing of an embodiment of a hydraulic rotate module.

The rotate module 510, FIG. 5A, comprises similar hydraulic components as those of the extend module 410. As in the extend module 410, hydraulic pressure, applied by rotating the control portion 110 along a longitudinal axis, causes piston 520 to move toward the distal end of the module, causing the shaft 518 to move in that direction as well. The shaft 518 is attached to a lead screw 522 at an attachment point 524. Extension of the shaft 518 causes the lead screw 522 to move towards the distal end of the module. The lead screw is incapable of rotating, since a stabilizer 526 prevents its rotation. The lead screw 522 instead is extended through a nut assembly 528 which is immovably attached to an outer cylinder 530. The movement of the lead screw 522 through the nut assembly 528 causes the nut assembly 528 to rotate, thereby rotating the outer cylinder 530.

Additional modules can be attached to the rotate module either at its distal end, through the distal attachment point 532, or at its proximal end, through the proximal attachment point 534.

Figure 5B:
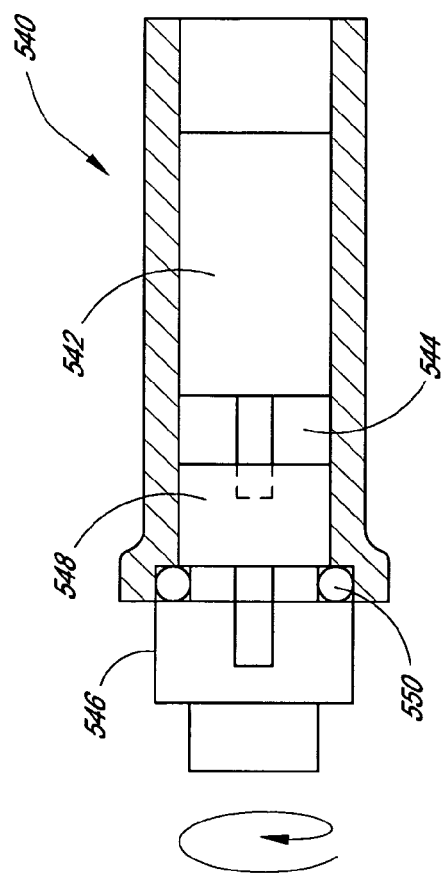
FIG. 5B is a detailed drawing of an embodiment of an electrical rotate module.

In another embodiment, the rotate module may be rotated using electrical power instead of hydraulic power. In this embodiment, by turning the handle 210 of the control portion 110, the user causes an electrical connection to be formed, whereby an electrical signal is sent from the control portion 110 through wires in the intermediate portion 190 to the rotate module 540, FIG. 5B. The electrical signal causes an electrical motor 542 to turn. The electrical motor 542 is attached to a shaft 544 which in turn is attached to the outer cylinder 546. The turning of the shaft rotates the outer cylinder. In some embodiments, a gear reducer assembly 548 may also be present to reduce the rotation speed. In certain embodiments, the connection between the outer cylinder 546 and the cylinder housing the motor assembly 542 may feature a bearing assembly 550.

Figure 6A:
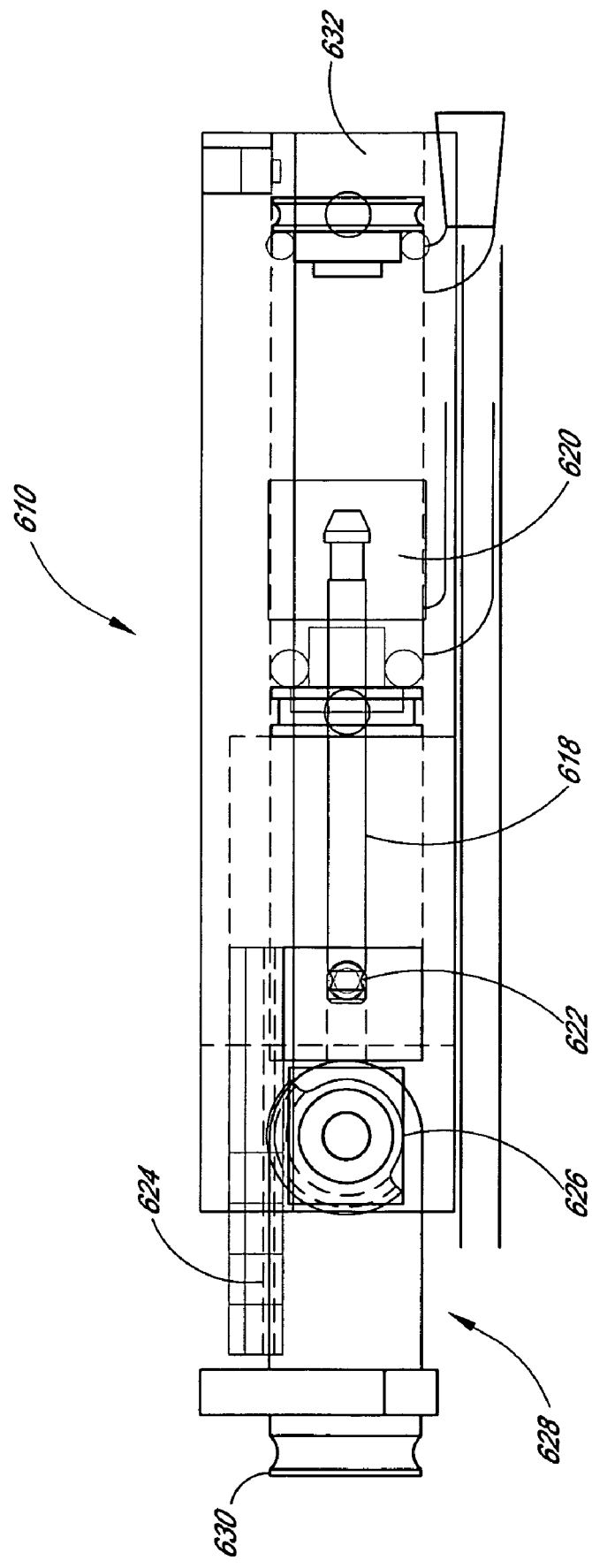
FIG. 6A is a detailed drawing of an embodiment of a hydraulic bend module.
Figure 6C:
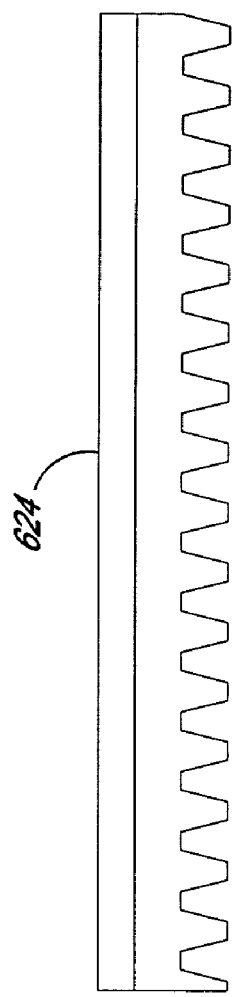
FIG. 6C is a drawing of a rack component in the module.
Figure 6B:
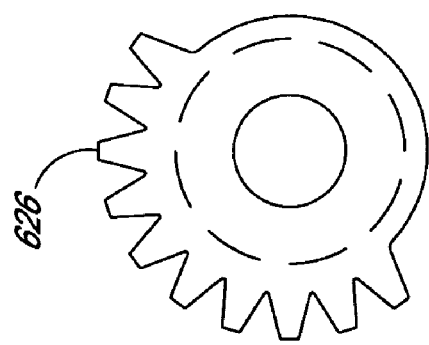
FIG. 6B is a drawing of a gear component in the module.

The bend module 610 is depicted in FIG. 6A. This module also features the same hydraulic assembly present in the extend and the rotate modules, above. Applying hydraulic pressure by rotating the control portion 110 along the vertical axis 226 in a clockwise direction causes the piston 620 and the shaft 618 to move towards the distal end of the module. The shaft 618 is attached to a rack 624 either directly or through an attachment assembly 622. The movement of the shaft 618 moves the rack 624. The rack 624 has teeth that correspond to the teeth on a gear 626. The movement of the rack 624 causes the gear 626 to rotate clockwise. The gear 626 is connected to the distal end 628 of the module. The rotation of the gear 626 causes the distal end 628 of the module to bend clockwise. By rotating the control portion 110 in a counter-clockwise direction, the piston 620 is moved towards the proximal end of the module, causing the rack 624 to move backwards as well, which in turn causes the gear 626 to turn counter-clockwise, which in turn causes the distal end 628 of the module to bend counter-clockwise.

In some embodiments, the bending of the distal end 628 of the module is through an angle of at least 110°, i.e., when the piston 620 moves from the proximal end of the hydraulic portion completely to the distal end of the hydraulic portion, the distal end 628 of the module bends at least 110°. In other embodiments, the rotation is an angle of at least 110°, at least 150°, at least 200°, at least 250°, at least 300°, or an angle of at least 350°.

Additional modules can be attached to the bend module either at its distal end, through the distal attachment point 630, or at its proximal end, through the proximal attachment point 632.

In another embodiment, the bend module may be bent using electrical power instead of hydraulic power. In this embodiment, by turning the handle 210 of the control portion 110, the user causes an electrical connection to be formed, whereby electrical signal is sent from the control portion 110 through wires in the intermediate portion 190 to the bend module. The electrical signal causes an electrical motor to turn. The electrical motor is attached to a shaft which in turn is attached to the rack 624. The movement of the shaft 618 moves the rack 624, which in turn causes the gear 626 to rotate, which in turn causes the distal end 628 of the module to bend.

Figure 6D:
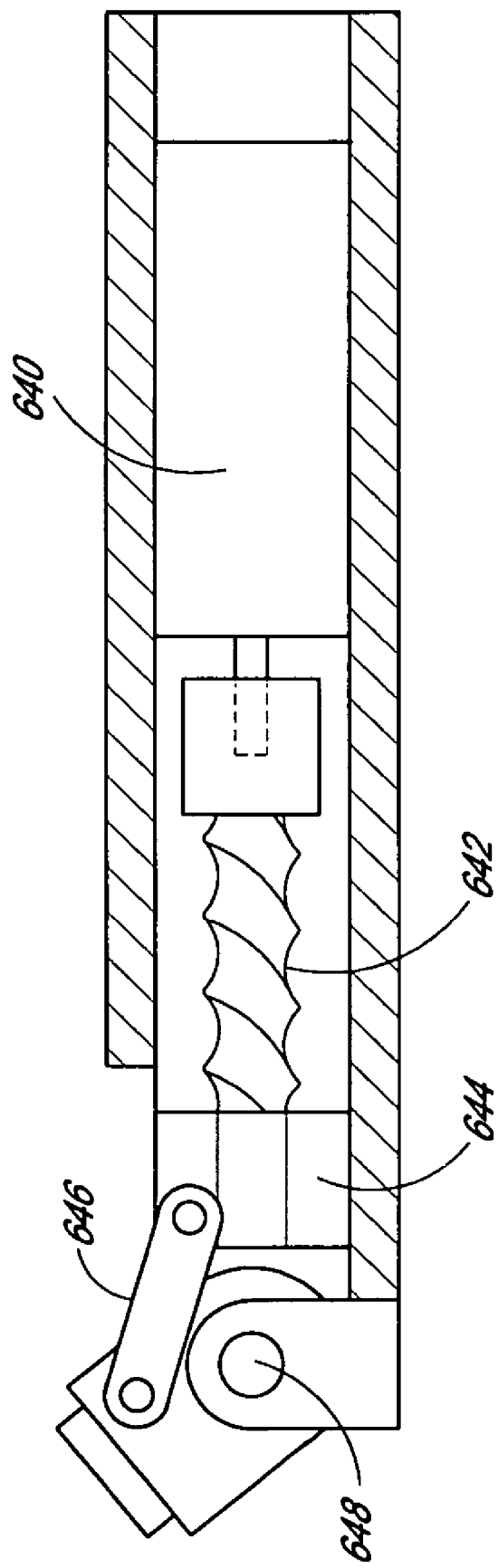
FIG. 6D is a detailed drawing of an embodiment of an electrical bend module.

In another embodiment, FIG. 6D, the turning of the motor 640 causes a lead screw 642 to rotate within a nut 644. The lead screw 642 is stationary with respect to the motor 640 and the outer body of the module, whereas the nut 644 is mobile. The nut 644 is connected to a link 646 at the proximal end of the link 646. The distal end of the link 646 is connected to the distal end of the module. When the nut 644 is moved backwards, it causes the link 646 to move backwards, thereby causing the distal end of the module to rotate. Reversing the electrical current, by rotating the control portion 110 in the opposite direction, will cause the motor to turn in the opposite direction, thereby causing the nut to move forward and the distal end of the module to bend in a clockwise direction.

Figure 7A:
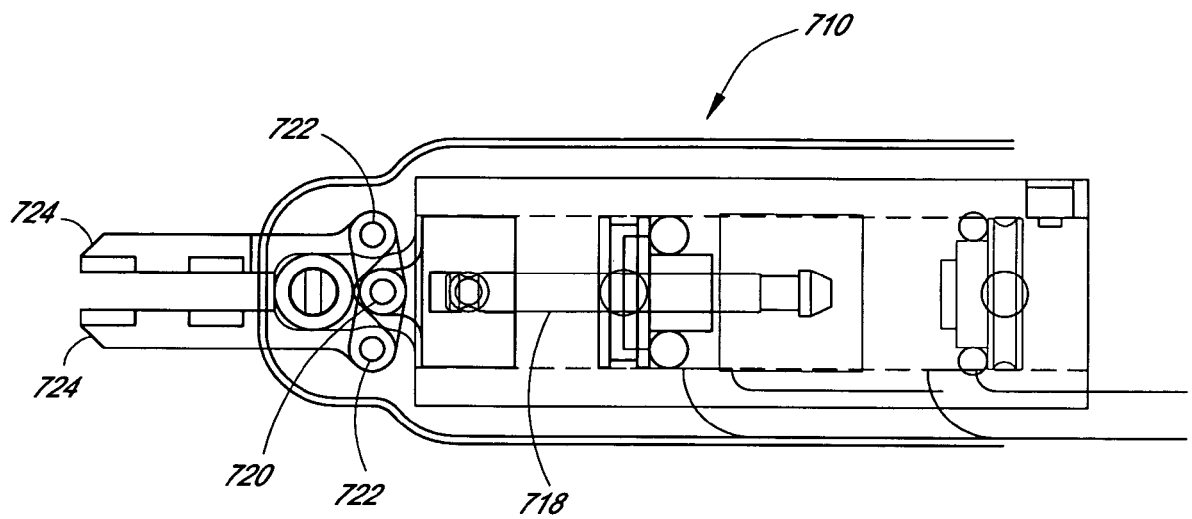
FIG. 7A-B is a detailed drawing of an embodiment of a hydraulic grasp module.
Figure 7B:
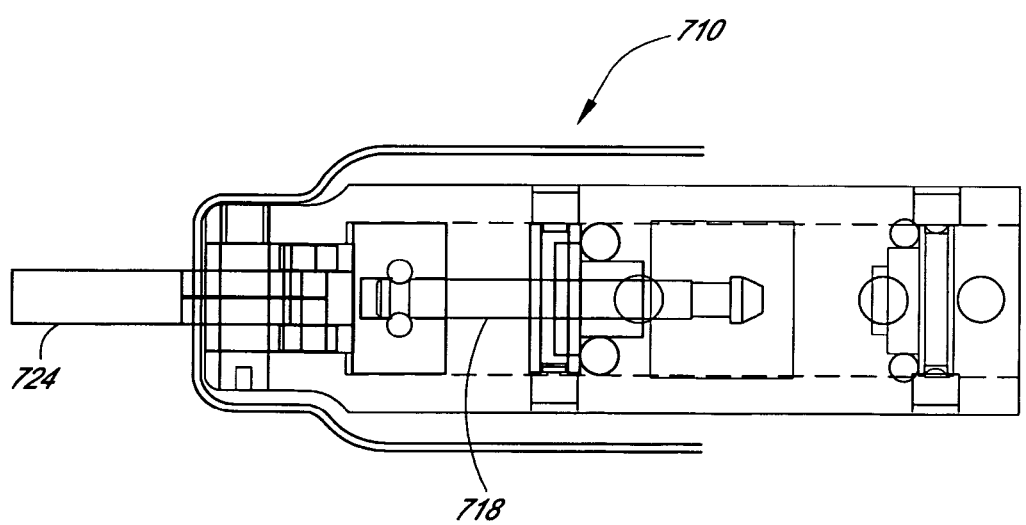

FIG. 7A depicts the top view of the grasp module 710, whereas FIG. 7B depicts its side view. The grasp module 710 also features a hydraulic portion similar to those of other modules. When the thumb loop 212 is squeezed towards the handle 210, hydraulic pressure is applied and the shaft 718 moves towards the distal end of the module. This movement causes the pin 720 to move towards the distal end of the module as well, thereby causing the two pins 722 to move away from the center. As the two pins 722 move away from the center, the angle defined by pin 722-pin 720-pin 722 tends away from 90° and towards 180°. The movement of the pins 722 causes the two tynes 724 to move towards each other and, eventually, touch. Moving the thumb loop 212 away from the handle 210 will have the opposite effect of causing the tynes 724 to move away from each other and open up.

Figure 7C:
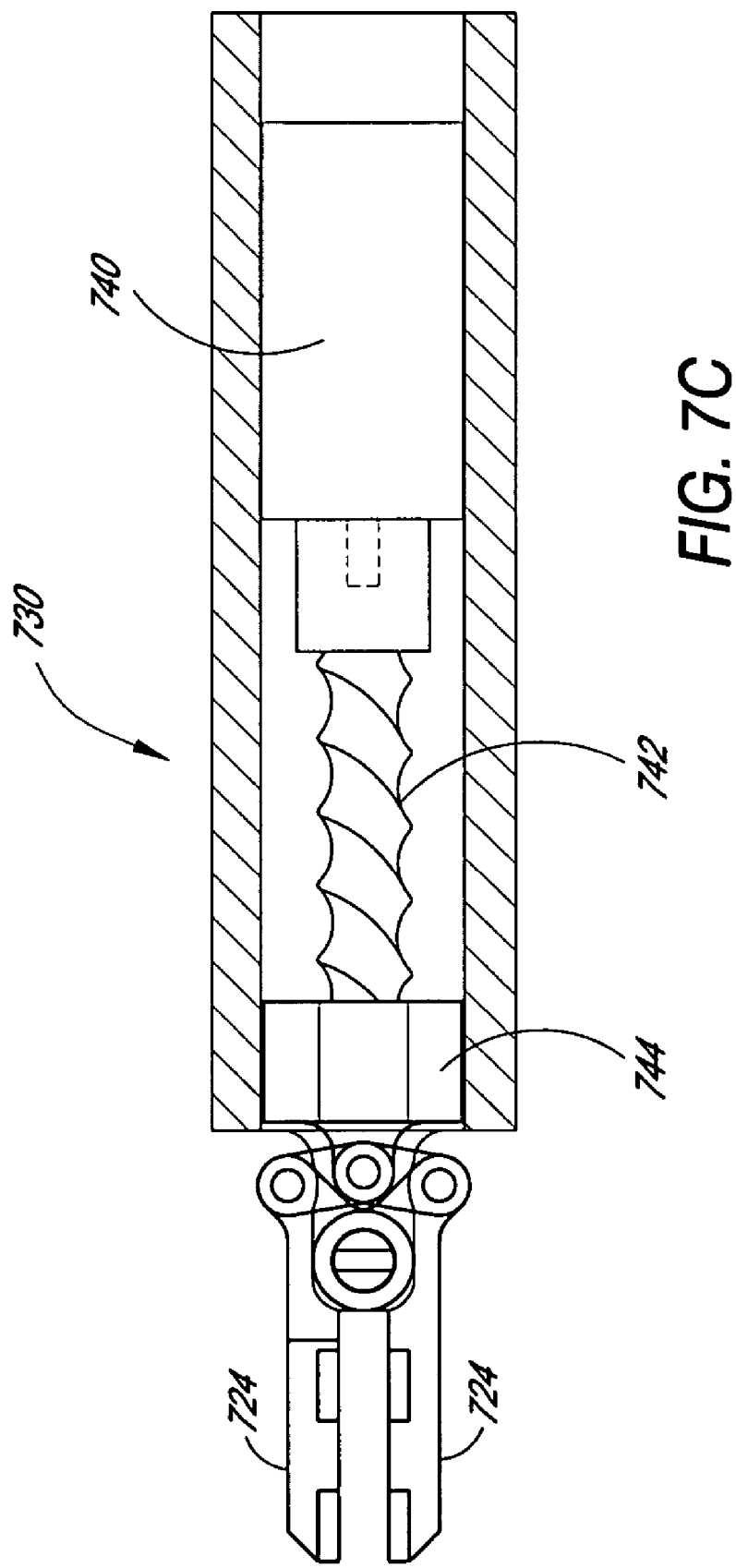
FIG. 7C is a detailed drawing of an embodiment of an electrical grasp module.

In another embodiment, the squeezing of the thumb loop 212 causes an electrical current to turn a motor 740, FIG. 7C, in the grasp module 730. The motor 740 turns a stationary lead screw 742, which in turn causes a nut 744 to move longitudinally. The movement of the nut 744 causes the tynes to move closer to each other and, eventually, touch. Moving the thumb loop 212 away from the handle 210 will have the opposite effect of causing the tynes 724 to move away from each other and open up.

Figure 8:
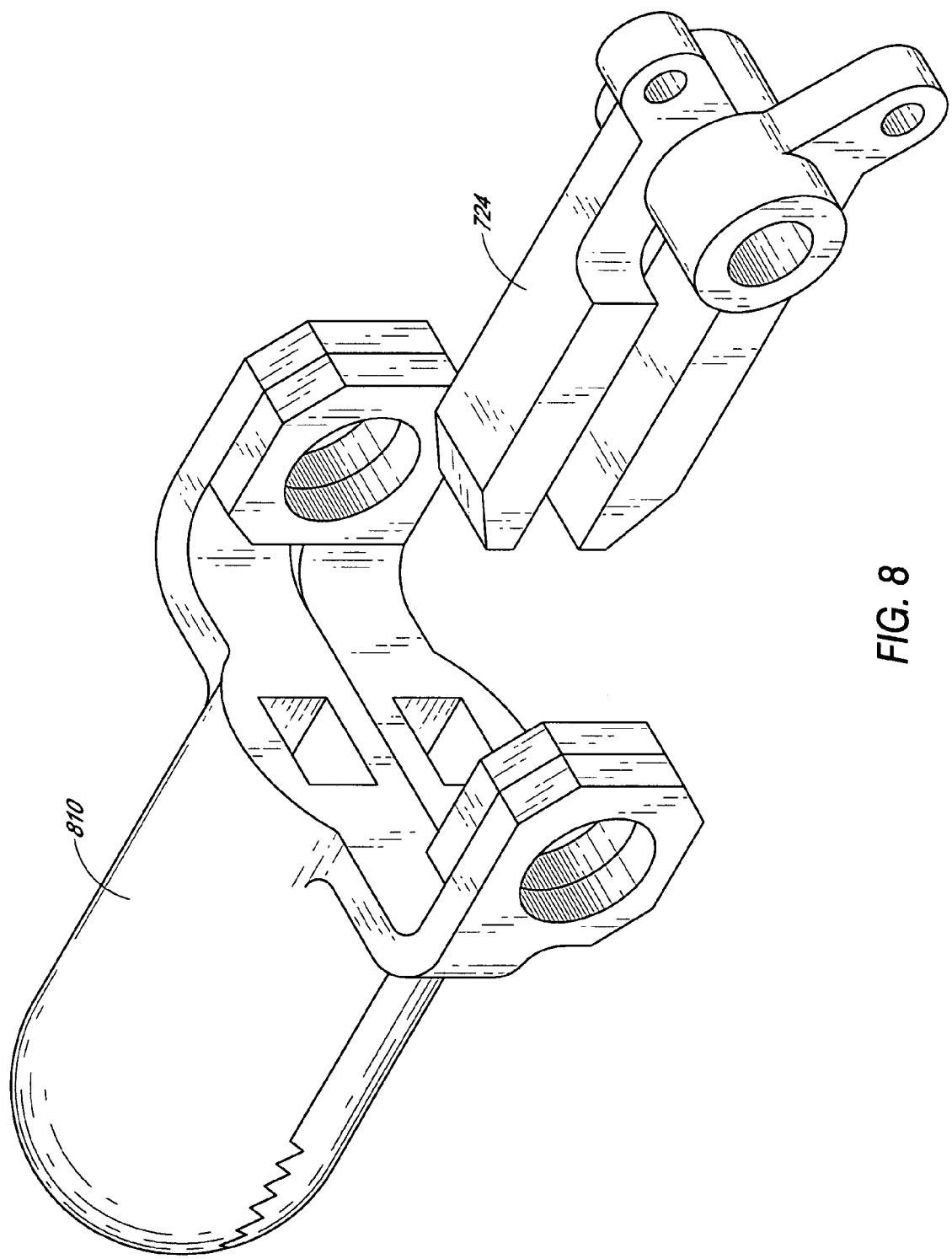
FIG. 8 depicts a tool adapted to fit over the tynes of a grasp module.

The tynes 724 of the grasp module 710 are configured to accommodate a number of different tools. For example, in FIG. 8, a grasp tool 810 is shown that can fit over the tynes 724. When the tynes 724 move towards each other, the end portion of the grasp tool 810 also move toward each other and, eventually, touch. If an object or tissue is located between the end portions of the grasp tool 810, the object is then grasped by the tool. There may be a number of tools that can be attached over the tynes 724. In addition to the grasp tool, these include a scissors, a knife for cutting the tissue, drill bits for drilling into bones, heating elements for cauterizing tissue, or any other tool necessary during a surgical procedure.

All the above tools and other tools can fit individually and interchangeably on the grasp module 710. Therefore, during a surgical procedure, the user may attach one tool to the grasp module 710, use it, remove it, and then attach another tool to the same grasp module 710. This process can be repeated any number of times with any number of tools.

Figure 9A:
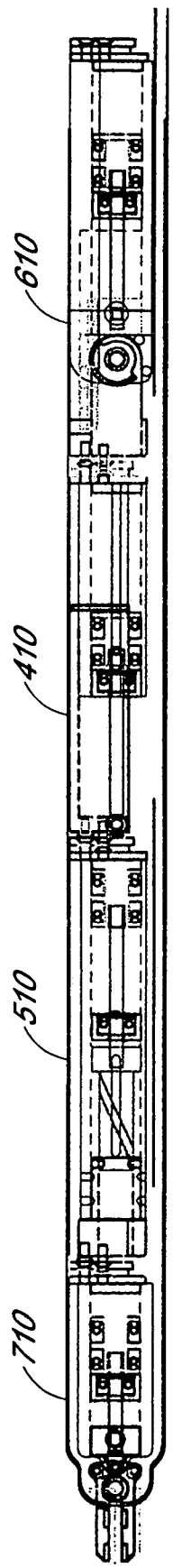
FIG. 9A shows the modules in bend-extend-rotate-grasp configuration, with the bend module in the straight conformation.
Figure 9B:
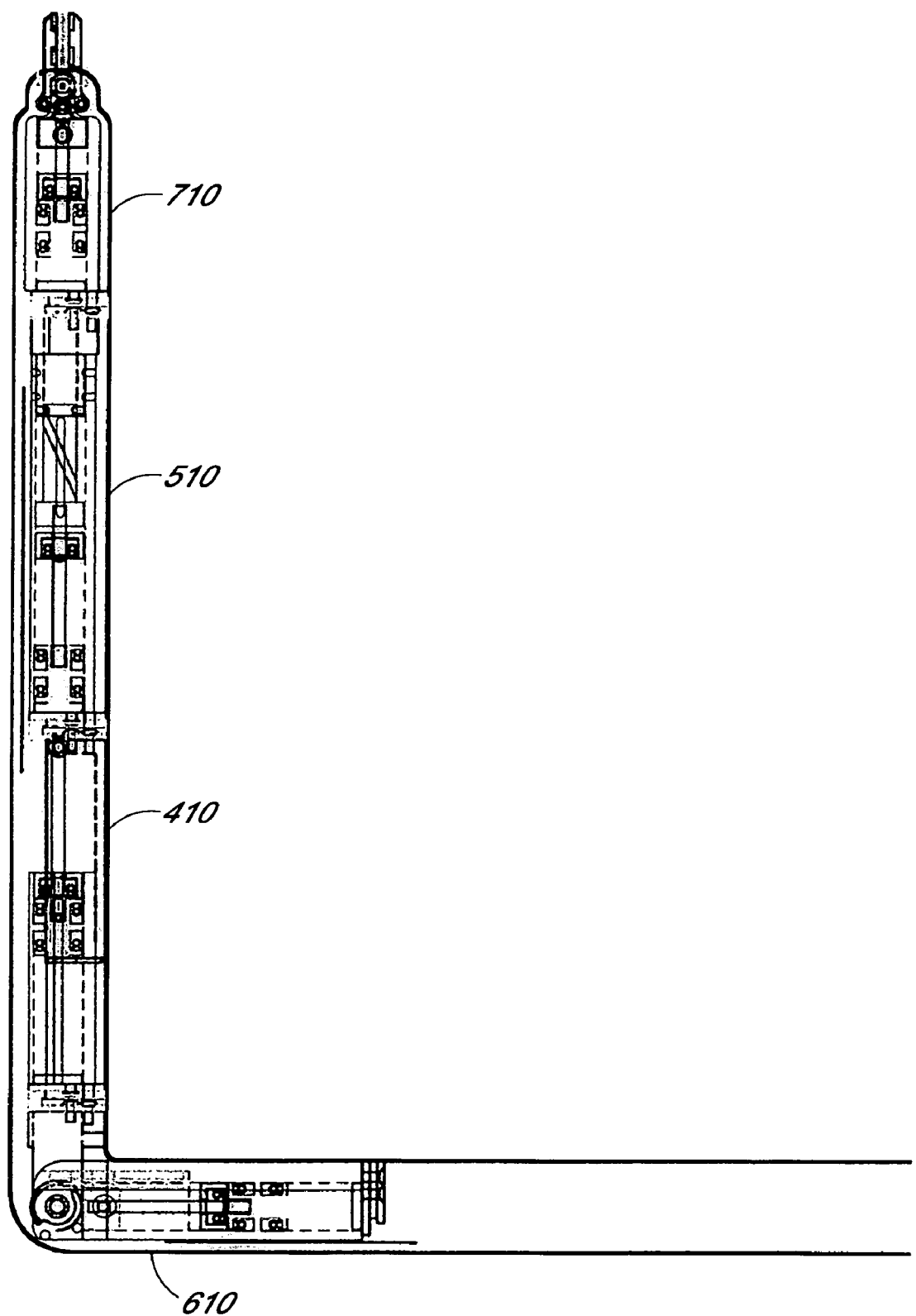
FIG. 9B shows the same arrangement with the bend module in the bent conformation.
Figure 9C:
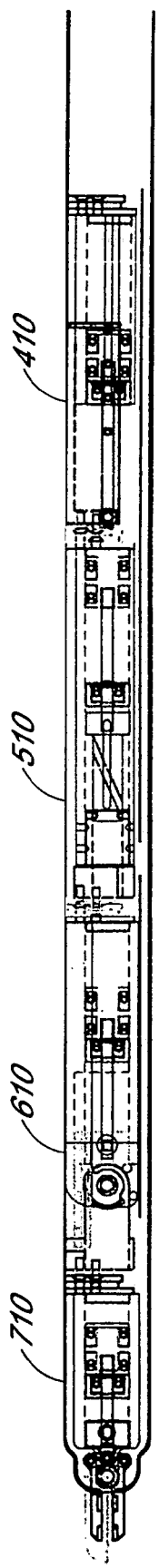
FIG. 9C shows the modules in extend-rotate-bend-grasp configuration, with the bend module in the straight conformation.
Figure 9D:
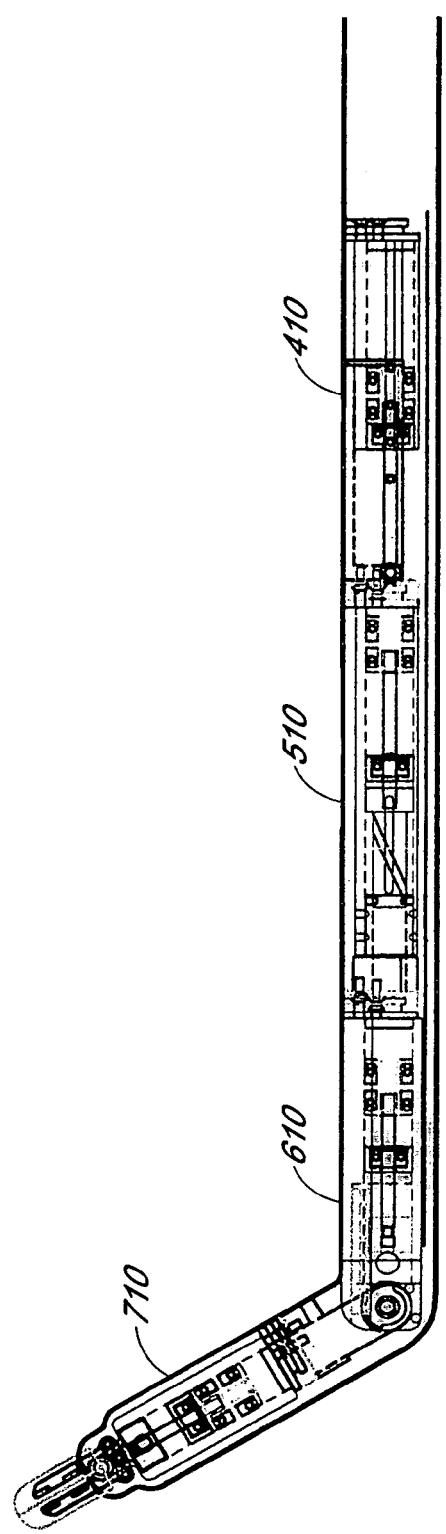
FIG. 9D shows the same arrangement with the bend module in the bent conformation.

As mentioned above, the modules of the present invention are designed to be placed in order that the user deems most useful. For example, FIG. 9 depicts four of the modules attached in the order of (from proximal end to distal end) bend, extend, rotate, and grasp. FIG. 9A shows the bend module in its retracted position, where the cannula is straight. FIG. 9B shows the bend module in its extended position where the module is bent. Alternatively, the four modules could be arranged in the extend-rotate-bend-grasp configuration, as shown in FIGS. 9C, 9D. Other combinations are also possible. In addition, the user may attach more than a single module of a particular type, for example, two or three or more extend modules or two or three or more bend modules, could be put together, along with other modules to form the distal end 120 of the device. Preferably, the grasp module 710 is always the most distally located module.

Figure 10A:
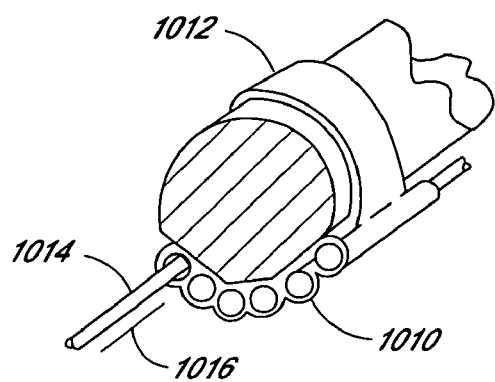
FIG. 10A shows the guide tubes as they are attached to the cannula using an elastic strap.
Figure 10B:
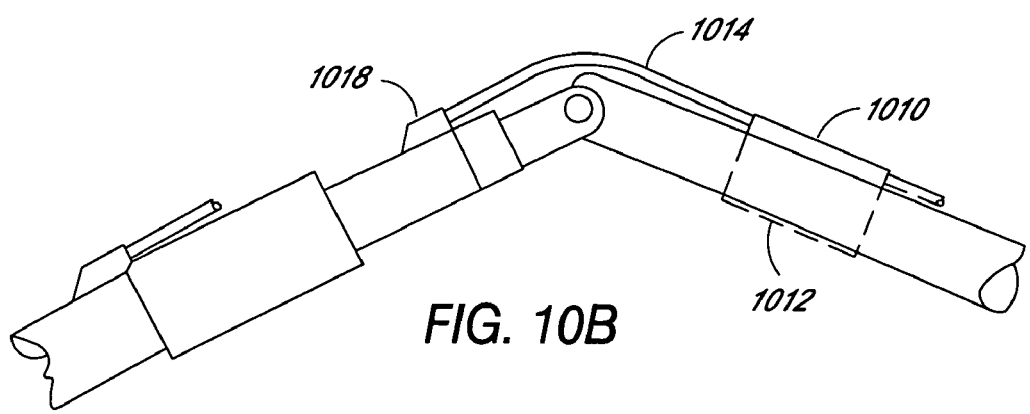
Figure 10C:
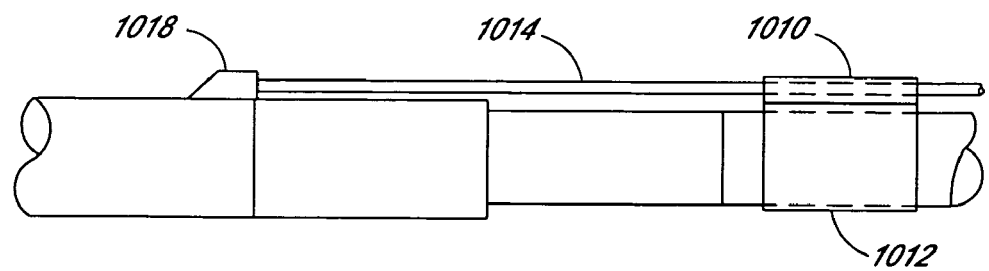
FIG. 10C shows the position of the guide tubes with respect to the extend module.

As shown in FIG. 4C, the front view of the extend module, the hydraulic tubing connecting the various modules to the control cylinders are located at one side of the slave cylinders. The hydraulic tubing runs alongside the cannula and connects to the inlet openings of the hydraulic portion of each module. In some embodiments of the invention, to keep the hydraulic tubing in place, a series of low friction guide tubes 1010 are attached to the cannula by an elastic strap 1012 (FIG. 10A). Each hydraulic tubing 1014 fits through one guide tubing and is free to move longitudinally, i.e., in the direction of the arrow 1016, within the guide tubing 1010. Thus, when the bend module bends, FIG. 10B, or when the extend module extends, FIG. 10C, the hydraulic tubing can move along the cannula and maintain the connection 1018 with the hydraulic inlets of each of the modules.

Figure 11A:
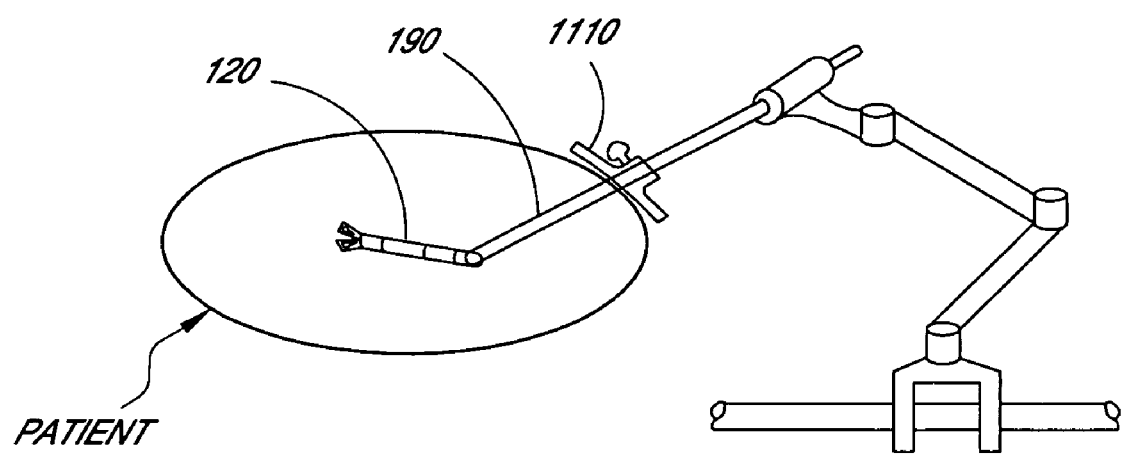
FIGS. 11A-B show an embodiment of the patient restraint.
Figure 11B:
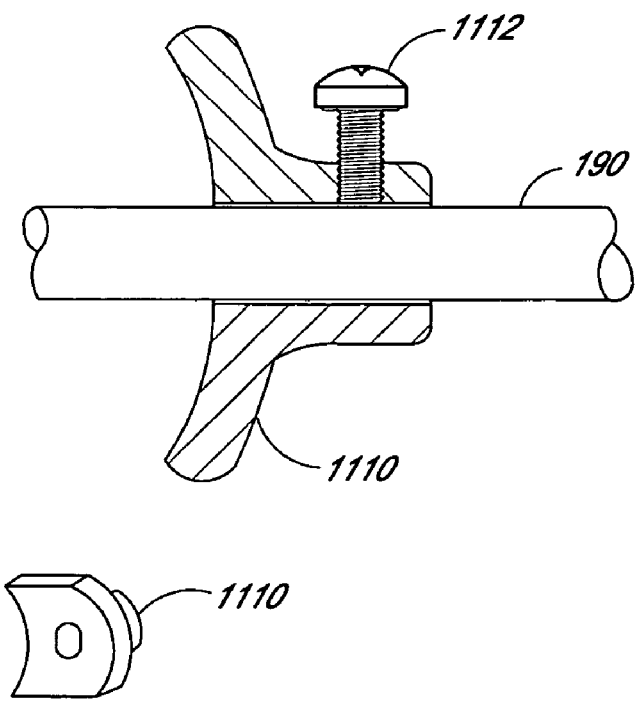

In certain embodiments, the present invention features a restraint 1110 that can be attached to the cannula 190 using a thumb screw 1112 (FIG. 11). The restraint 1110 sits adjacent to the patient's skin on the outside of the patient's body at the point of entry of the cannula 190. The restraint 1110 keeps the depth of the cannula 190 with respect to the body of the patient's body. If the patient makes any moves during the surgery, for example if the anesthesia begins to wear off and the patient jolts, the cannula moves with the patient. More importantly, the depth of the cannula inside the patient's body remains unchanged. Therefore, if the patient moves, the patient will not be damaged by the cannula.

As part of their normal physiological function, certain organs in the body have continuous motion. For example, the heart beats, the lungs expand and contract as the patient breathes, and the gastrointestinal tract also undergoes contractile motion. When performing surgery, it is often necessary stabilize the part of the organ undergoing surgery so that additional injury to the organ does not occur and the organ can be worked on. Aspects of the invention also feature a tissue restraint module 1210 (FIG. 12) that can be inserted into the patient's body at or near the site where any other cannula has been inserted. The tissue restraint module 1210 features a bend module, as described above. Once inserted into the patient's body, the separable tynes 1214 can be brought close to the tissue that is to be restrained. The bend module allows the tyne assembly to be bent with respect to the cannula, so that the tynes 1214 may be placed over the tissue. The tynes 1214 are separable so that they can provide a relatively stable tissue area for the performance of the surgery.

A number of different mechanisms for separating the tynes 1214 are shown in FIGS. 12C-E. In the embodiments shown, the tissue restraint module comprises two tynes 1214. The tynes 1214 are adapted to be separable. When inserting the module into the patient's body, the tynes 1214 are held together to reduce the width of the device. Inside the patient's body, the tynes 1214 can be separated. In the embodiment shown in FIG. 12C, one tyne 1214 is stationary, while the second tyne 1214 slides away from the first tyne 1214. In the embodiment shown in FIG. 12D, both tynes 1214 move away from the center. Since the two tynes 1214 are bent inward, in their fully extended position the distal end of the two tynes 1214 would be parallel to each other. The embodiment shown in FIG. 12E functions similarly, except that the two tynes are not bent. In the fully extended position the two tynes 1214 form a "V" shaped opening. Other embodiments are also contemplated. For example, the tissue restraint module may comprise only one tyne. In certain embodiments, the single-tyne module may have a shape such as "∩", "[", or "⊤".

In certain embodiments, the tissue restraint module is held against a tissue or an organ during the surgical procedure. By doing so, in the space between the two tynes 1214, or a particular space created within a single tyne, a surface area of the tissue or organ becomes restrained, i.e., the local motion of the tissue or the organ is considerably reduced as compared with an unrestrained region of the tissue or the organ. The restraining of the tissue or the organ provides a relatively stable area on which the user can perform the surgical procedure.

In certain embodiments, the intermediate portion 190 of the cannula can be adapted to hold a number of different tools to be used during the operation. The cannula may be the cannula leading to the tissue restraint module or the cannula leading to the grasp module 710 at the distal end 120 of the device. Preferably, the cannula is the one leading the tissue restraint module. During the operation, the user can retrieve a first tool from the cannula while within the patient's body and attach it to the grasp module 710. After using the first tool, the user can then return the first tool to the cannula, retrieve a second tool and attach it to the grasp module 710. Other tools may subsequently be used in a similar fashion.

The cannula 190 is held in place using a positioning arm 140 (see FIG. 1). The positioning arm 140 comprises at least one joint capable of being tightened or loosened using a release mechanism. The user can release the joint, move the positioning arm 140 to a desired location, and thereby reposition the cannula 190. In one embodiment, the invention provides for a one-hand-release mechanism. In this embodiment, the user can grasp the positioning arm 140 with one hand, and while holding the positioning arm 140, loosen the joint using the same hand, move the positioning arm 140 to a new location using the same hand, and then tighten the joint, again using the same hand. The one-hand-release mechanism allows the user to reposition the cannula using one hand, while manipulating the distal end 120 of the device using the control portion 110 with the other hand.

In using the devices of the present invention, it is often the case that the tools at the distal portion of the device are to move a short distance. This distance is small enough that it would become difficult for the user to move his hands or fingers for that short a distance. Therefore, a system is needed to convert a longer movement of the user's hands and fingers at the proximal end of the device to a short movement of the tools at the distal end of the device. This is accomplished by having the control cylinder and the slave cylinder be of different diameters. Of importance, is the relationship between the piston area and the shaft area when using cylinders of different diameters, as generally described below.

Figure 16A:
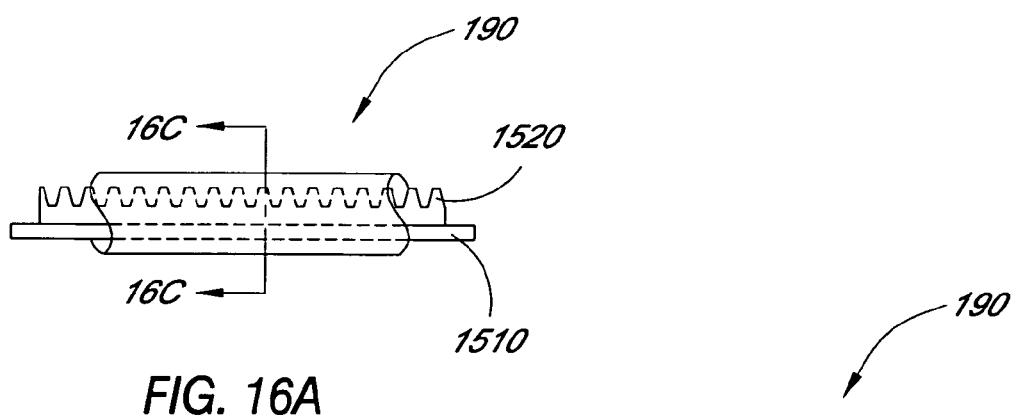
FIGS. 16A-C are side views showing the articulation mechanism of FIGS. 15A-B in greater detail.
Figure 16B:
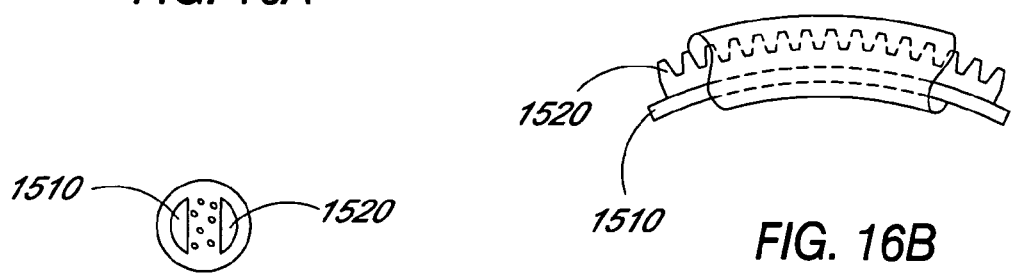
Figure 16C:
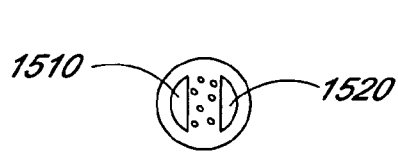

At least a portion of the intermediate portion 190 of the laparoscopic tool is preferably an articulation portion. FIGS. 15A-B and 16A-C illustrate one embodiment of an articulation mechanism implemented in the articulation portion of the intermediate portion 190. A spring bar 1510 is embedded within the body of the outer sleeve. The spring bar may be made of any material, such as plastic or metal, that allows it to resiliently bend while exerting a reacting force against the bending. The spring bar 1510 acts to prevent the articulation portion from bending unless a force is exerted to cause it to bend. An opposite wall of the sleeve is lined with small pouches 1520. FIG. 16C illustrates the arrangement of the pouches 1520 and the spring bar 1510 in a cross-sectional view of the articulation portion. The pouches 1520 are densely placed along the length of the articulation portion. The pouches 1520 are connected to a reservoir of hydraulic liquid (not shown) by a series of orifices or valves in each pouch. When hydraulic fluid is supplied to the pouches 1520 through the orifices or valves, the pouches 1520 are filled with the hydraulic liquid. The filled pouches 1520 press against one another and force an expansion of the side of the articulation portion with the pouches 1520. This expansion causes the spring bar 1510 to bend, causing the articulation portion to bend, as shown in FIG. 16B.

Double Acting/Double Cylinder System

Figure 13:
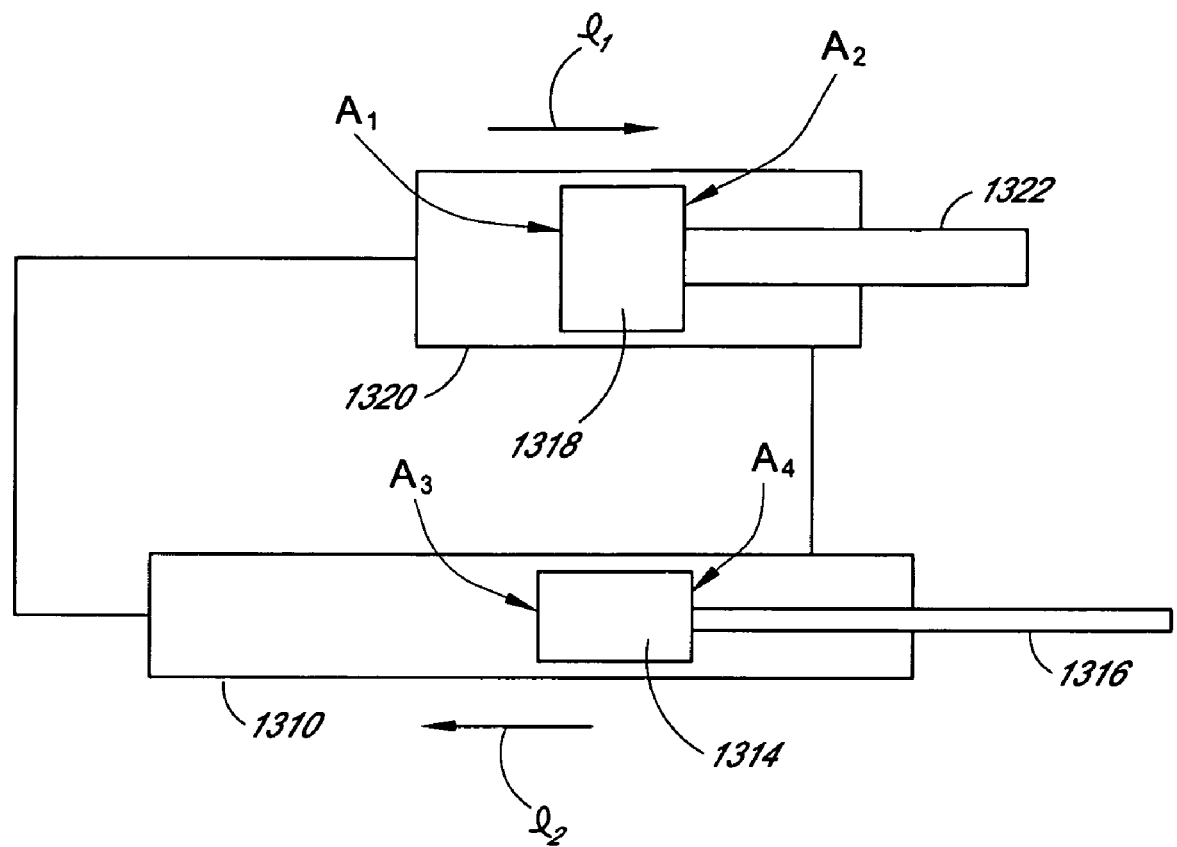
FIG. 13 shows the different cylinder diameters for changing the ratio of movement between the control cylinder and slave cylinder.

Another aspect of the present invention includes a double acting/double cylinder system. This system is depicted in FIG. 13. The system comprises a control cylinder 1320 and a slave cylinder 1310. The control cylinder comprises a piston 1318 and a shaft 1320 attached thereto. The piston 1318 is capable of moving within the control cylinder 1320. The piston divides the control cylinder into two cavities: a distal cavity, a wall of which is $A_1$, and a proximal cavity, a wall of which is $A_2$. The shaft 1322 passes through the proximal cavity. The piston 1318 prevents liquid communication between the distal cavity and the proximal cavity.

The slave cylinder comprises a piston 1314 and a shaft 1316 attached thereto. The piston 1314 is capable of moving within the slave cylinder 1310. The piston divides the slave cylinder into two cavities: a distal cavity, a wall of which is $A_3$, and a proximal cavity, a wall of which is $A_4$. The shaft 1316 passes through the proximal cavity. The piston 1314 prevents liquid communication between the distal cavity and the proximal cavity.

A control line provides hydraulic communication between the proximal cavity of the control cylinder and the proximal cavity of the slave cylinder. Another control line provides hydraulic communication between the distal cavity of the control cylinder and the proximal cavity of the slave cylinder. Thus, in the system, the two distal cavities are in hydraulic communication with each other, the two proximal cavities are in hydraulic communication with each other, but no proximal cavity is in hydraulic communication with any distal cavity.

If the control cylinder piston 1318 moves towards the distal end of the control cylinder 1320, hydraulic fluid is moved from the distal cavity of the control cylinder, through a control line, and into the distal cavity of the slave cylinder, thereby pushing the slave cylinder piston 1314 towards the proximal end of the slave cylinder 1310. The reverse may also happen. If the control cylinder piston 1318 moves towards the proximal end of the control cylinder 1320, hydraulic fluid is moved from the proximal cavity of the control cylinder, through a control line, and into the proximal cavity of the slave cylinder, thereby pushing the slave cylinder piston 1314 towards the distal end of the slave cylinder 1310. Further, while the control cylinder piston 1318 remains stationary, the salve cylinder piston 1314 also remains stationary.

In an embodiment, the double acting/double cylinder system of the invention comprises an overpressure reservoir. If the hydraulic pressure within the cylinders or the control lines exceeds a certain amount, some hydraulic fluid is transferred to the overpressure reservoir. The opening to the overpressure reservoir may comprise a pressure gauge device, which can become activated when the hydraulic pressure within a system surpasses a certain preset value. When the pressure gauge device is activated, the opening to the overpressure reservoir opens and hydraulic fluid can then enter the reservoir.

In another embodiment, the overpressure reservoir comprises an opening, which is in constant fluid communication with the hydraulic fluid within the system. The reservoir further comprises a spring mechanism at the side opposite to the opening. When the hydraulic pressure within the system surpasses the pressure applied by the spring mechanism, hydraulic fluid enters the reservoir from the system. Conversely, when the pressure within the system falls below the pressure applied by the spring mechanism, for example due to a leak in the system, hydraulic fluid enters the system from the reservoir. Thus, the reservoir may also function as a fluid replacement reservoir.

In certain embodiments, the flow of the hydraulic fluid inside the system will move very easily so that not enough resistance is afforded. In these situations, it is difficult for a user to control the movement of the cylinders with fine precision. Therefore, certain embodiments of the invention feature a narrowing at a point in the hydraulic tubing, the purpose of which is to create resistance. In some embodiments, the user can change the amount of narrowing, and therefore, the amount of resistance in the hydraulic tubing.

FIG. 13 depicts the relationship between the control cylinder 1310 and the slave cylinder 1312. The control cylinder 1310 has a piston 1314 and a shaft 1316. The front of the piston 1314, i.e., the opposite face from where the shaft 1316 attaches to the piston 1314, has an area of $A_3$ and the back of the piston 1314, i.e., the face where the shaft 1316 attaches, has an area is $A_4$. Thus, $A_3$ is equal to $A_4$ plus the area of the shaft 1316. When the piston 1314 moves backwards a distance of $l_2$, the amount of hydraulic fluid displaced in front of the piston 1314 will have a volume of $A_3 l_2$. However, the volume of the hydraulic fluid displaced behind the piston 1314 will be $A_4 l_2$.

The slave cylinder 1312 also has a piston 1318 and a shaft 1320. The volumes of displaced hydraulic fluid in front of and behind the piston 1318 must be equal to the volume of displaced hydraulic fluid in front of and behind the piston 1314. In other words, $$A_1 l_1 = A_3 l_2$$

and $$A_2 l_1 = A_4 l_2$$

where $l_1$ is the distance traveled by the slave cylinder. Rearranging the equations results in $$l_2 = \frac{A_1 l_1}{A_3} = \frac{A_2 l_1}{A_4}$$

which result in the basic relationship between the various surface areas as $$\frac{A_1}{A_3} = \frac{A_2}{A_4}$$

It is readily understood by those of skill in the art that the above relationship will also hold true if the control cylinder and the slave cylinder are configured such that small movements by the user's hands and fingers results in longer movements at the distal end of the device. In other words, in FIG. 13, in one embodiment 1312 represents the slave cylinder and 1310 represents the control cylinder, whereas in another embodiment, 1312 represents the control cylinder and 1310 represents the slave cylinder.

Figure 14:
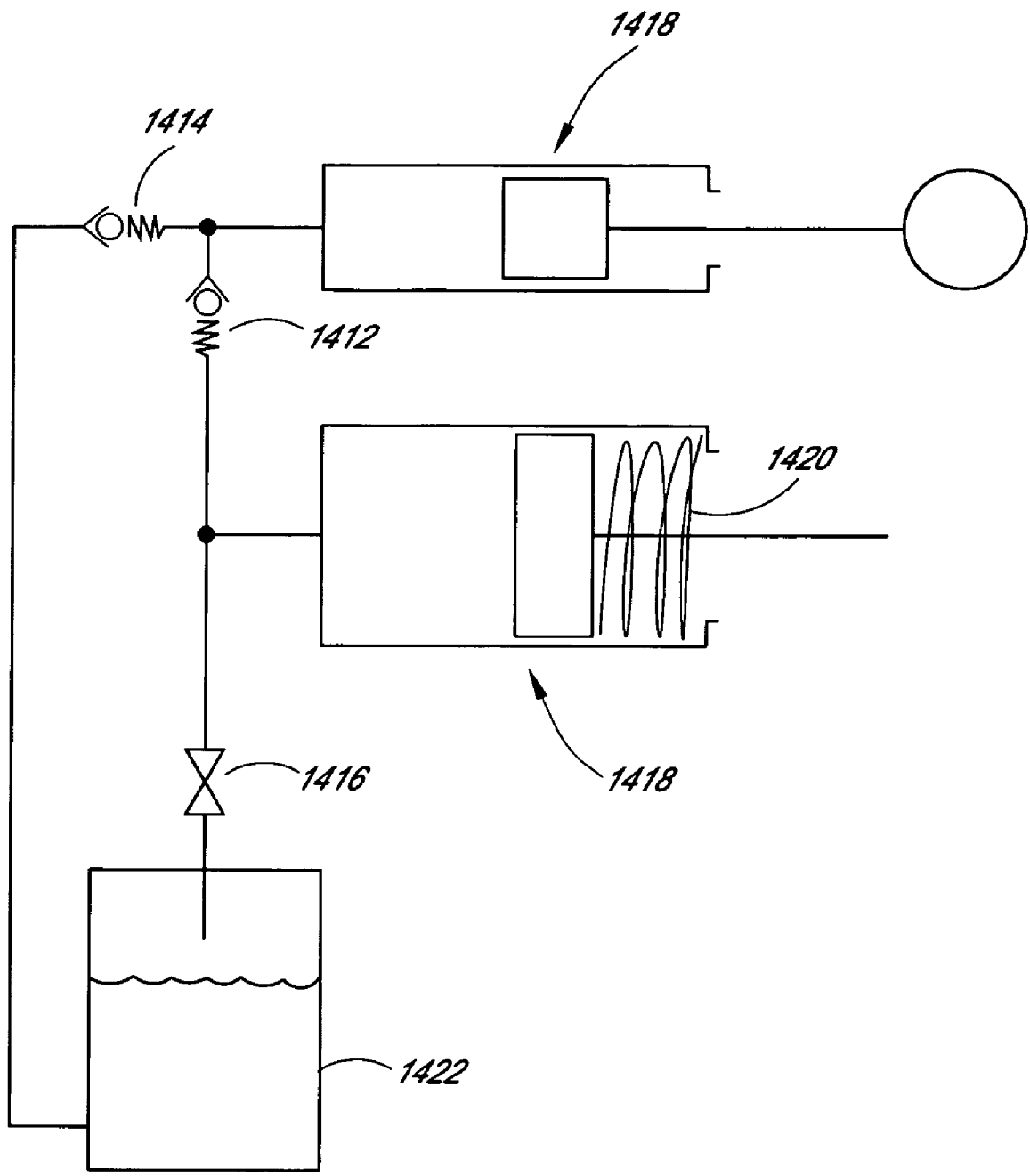
FIG. 14 shows an embodiment of the multiple stroke cylinder.
Figure 15A:
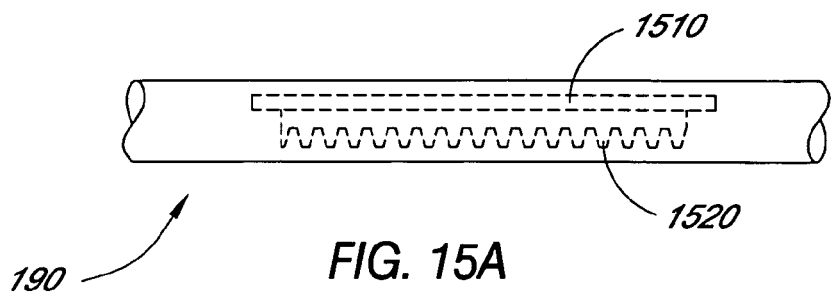
FIGS. 15A-B are side views showing the articulation mechanism of the present invention.
Figure 15B:
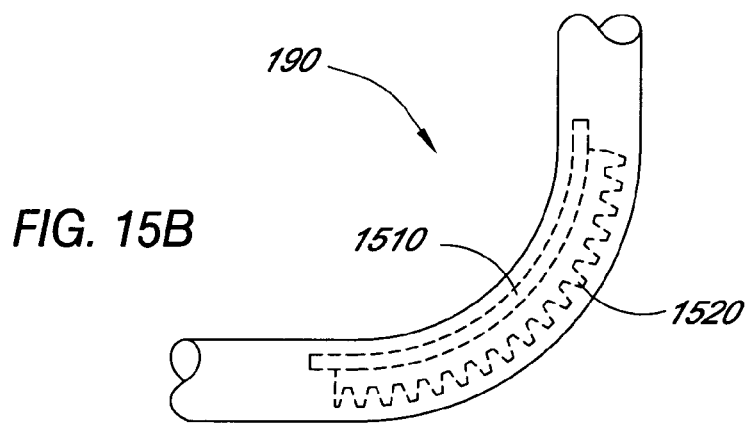

In certain embodiments, when it is desirable to have a long range of movement or very fine movement at the distal end of the device, it is preferable to affect a full range of movement at a slave cylinder at the distal end of the device using multiple strokes of a control cylinder. In these embodiments, the present invention features a multiple stroke cylinder system (FIG. 14). A stroke of the control cylinder 1410 causes check valve 1414 to close and check valve 1412 to open. Hydraulic fluid is then transferred from the control cylinder 1410 to the slave cylinder 1418. Returning the piston of the control cylinder 1410 to the original position, i.e., at the proximal end of the control cylinder, causes the check valve 1412 to close and the check valve 1414 to open. Additional hydraulic fluid is then transferred from the reservoir 1422 to the control cylinder 1410. Another stroke of the control cylinder 1410 will then cause additional movement in the slave cylinder 1418.

The system is also equipped with a "dump" valve 1416. The dump valve 1416 may be activated by the user at anytime. When the dump valve 1416 is activated, hydraulic fluid is transferred from the slave cylinder 1418 back to the reservoir 1422.

In some embodiments, to aid the removal of the hydraulic fluid from the slave cylinder 1418 a spring mechanism 1420 is placed behind the piston of the slave cylinder. Those of skill in the art know of other mechanisms that can be used to return the piston of the slave cylinder to its original position.

In other embodiments, the system is so configured that the user can reverse the flow of the hydraulic fluid. Therefore by additional strokes of the control cylinder the user can remove hydraulic fluid from the slave cylinder 1418 and transfer it back to the reservoir 1422.

CONCLUSION

Thus, those of skill in the art will appreciate that the devices described herein provide a relatively easy and economical instrument to perform minimally invasive surgery.

One skilled in the art will appreciate that these devices are and may be adapted to carry out the objects and obtain the ends and advantages mentioned, as well as those inherent therein. The methods, procedures, and devices described herein are presently representative of preferred embodiments and are exemplary and are not intended as limitations on the scope of the invention. Changes therein and other uses will occur to those skilled in the art which are encompassed within the spirit of the invention and are defined by the scope of the disclosure.

It will be apparent to one skilled in the art that varying substitutions and modifications may be made to the invention disclosed herein without departing from the scope and spirit of the invention.

Those skilled in the art recognize that the aspects and embodiments of the invention set forth herein may be practiced separate from each other or in conjunction with each other. Therefore, combinations of separate embodiments are within the scope of the invention as disclosed herein.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions indicates the exclusion of equivalents of the features shown and described or portions thereof. It is recognized that various modifications are possible within the scope of the invention disclosed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the disclosure.

What is claimed is:

1. A double cylinder system, comprising:
   at least one controller being adapted to transmit hydraulic control signals, said controller further comprises:
   a control cavity; and
   a first piston within said control cavity, said first piston dividing said control cavity into a first control cavity portion and a second control cavity portion and preventing communication between said first control cavity portion and said second control cavity portion;
   at least one slave being in fluid communication with said controller and being configured to respond to said hydraulic control signals transmitted by said controller, said slave comprising
   a slave cavity; and
   a second piston within said slave cavity, said second piston dividing said slave cavity into a first slave cavity portion and a second slave cavity portion and preventing communication between said first slave cavity portion and said second slave cavity portion; wherein said slave cavity is a part of a modular component selected from the group consisting of an extend module, a rotate module, a bend module, and a grasp module, wherein any one of said modules is capable of being used in combination with any other of said modules; and
   at least one control line providing hydraulic communication between said first control cavity portion and said first slave cavity portion; and
   at least one control line providing hydraulic communication between said second control cavity portion and said second slave cavity portion.

2. The system of claim 1, further comprising an overpressure reservoir.

3. The system of claim 1, further comprising a manipulator, wherein said manipulator is adapted to change the position of said first piston within said control cavity.

4. A surgical device, comprising:
   at least one controller located at a proximal end of the device, said controller being adapted to transmit hydraulic control signals;
   at least one manipulator, said manipulator being configured to be controlled by a human hand and to actuate said controller;
   at least one slave located at a distal end of the device, said slave being in fluid communication with said controller and being configured to respond to said hydraulic control signals transmitted by said controller; wherein said slave is a part of a modular component selected from the group consisting of an extend module, a rotate module, a bend module, and a grasp module, wherein any one of said modules is capable of bug used in combination with any other of said modules; and
   at least one control line providing hydraulic communication between said controller and said slave.

5. The surgical device according to claim 4, wherein said controller further comprises:
   a control cavity; and
   a piston within said control cavity, said piston dividing said control cavity into a first control cavity portion and a second control cavity portion and preventing communication between said first control cavity portion and said second control cavity portion;
   wherein said slave further comprises:
   a slave cavity; and
   a piston within said slave cavity, said piston dividing said slave cavity into a first slave cavity portion and a second slave cavity portion and preventing communication between said first slave cavity portion and said second slave cavity portion; and
   wherein said control line provides hydraulic communication between said first control cavity portion and said first slave cavity portion.

6. The surgical device according to claim 5, further comprising a second control line providing hydraulic communication between said second control cavity portion and said second slave cavity portion.

7. A surgical device, comprising:
   a control portion located at a proximal end of the device, comprising:
   a plurality of controllers, each of said plurality of controllers being adapted to transmit hydraulic control signals; and
   a plurality of manipulators, each of said plurality of manipulators being configured to actuate a corresponding one of said plurality of controllers;
   a slave portion located at a distal end of the device, comprising:
   a plurality of slaves, of said plurality of slaves being in communication with a corresponding one of said plurality of controllers and being configured to respond to said hydraulic control signals transmitted by said corresponding one of said plurality of controllers; wherein each of said plurality of slaves is a part of a modular component selected from the group consisting of an extend module, a rotate module, a bend module, and a grasp module, wherein any one of said modules is capable of being used in combination with any other of said modules; and
   an intermediate portion, comprising a plurality of control lines, each of said plurality of control lines providing communication with one of said plurality of controllers and a corresponding one of said plurality of slaves.

8. The surgical device according to claim 7, wherein said intermediate portion further comprises an outer sleeve enveloping said plurality of control lines.

9. The surgical device according to claim 7, wherein said intermediate portion further comprises an articulating portion, said articulating portion further comprising:
   a spring bar on a first side of said articulating portion; and
   a plurality o pockets on a second side of said articulating portion, said second side opposing said first side,
   wherein said pockets are configured to receive a hydraulic fluid, and
   wherein, said pockets am configured to expand when said hydraulic fluid is received.

10. The surgical device of claim 7, further comprising a tip adapted to be manipulated by at least one of said plurality of slaves in response to said hydraulic control signals.

11. The surgical device of claim 7, wherein said hydraulic communication is through a hydraulic fluid.

12. The surgical device of claim 11, wherein said hydraulic fluid is physiologically acceptable.

13. The surgical device of claim 7, wherein each of said plurality of slaves has a predefined function.

14. The surgical device of claim 13, wherein said predefined function is selected from extension, rotation, bending, and grasping.

15. The surgical device of claim 13, wherein said predefined function of at least one of said plurality of slaves is different than said predefined function of at least another one of said plurality of slaves.

\* \* \* \* \*